US008389521B2

(12) United States Patent
Schauerte et al.

(10) Patent No.: US 8,389,521 B2
(45) Date of Patent: *Mar. 5, 2013

(54) INHIBITORS OF PROTEIN KINASES

(75) Inventors: Heike Schauerte, Munich (DE); Hans Allgeier, Loerrach-Haagen (DE); Michael A. Pleiss, Sunnyvale, CA (US); Martin Augustin, Seefeld-Hechendorf (DE); Gisela Peraus, Loerrach (DE); Gabriele Stumm, Unterhaching (DE); Philipp Wabnitz, Dusseldorf (DE)

(73) Assignee: Ingenium Pharmaceuticals GmbH, Martinsried (DE)

( * ) Notice: Subject to any disclaimer, the term of this patent is extended or adjusted under 35 U.S.C. 154(b) by 354 days.

This patent is subject to a terminal disclaimer.

(21) Appl. No.: 12/451,040

(22) PCT Filed: Apr. 24, 2008

(86) PCT No.: PCT/EP2008/054972
§ 371 (c)(1),
(2), (4) Date: Mar. 26, 2010

(87) PCT Pub. No.: WO2008/129069
PCT Pub. Date: Oct. 30, 2008

(65) Prior Publication Data
US 2010/0184780 A1    Jul. 22, 2010

(30) Foreign Application Priority Data
Apr. 24, 2007 (WO) ................. PCT/EP2007/003604

(51) Int. Cl.
C07D 239/42 (2006.01)
C07D 403/10 (2006.01)
A61K 31/505 (2006.01)

(52) U.S. Cl. ................ 514/235.8; 514/252.14; 514/256; 544/122; 544/295; 544/326; 544/327; 544/328

(58) Field of Classification Search .................. 544/122, 544/295, 326, 327, 328; 514/235.8, 252.14, 514/256
See application file for complete search history.

(56) References Cited

U.S. PATENT DOCUMENTS

| 5,908,848 | A  | 6/1999 | Miller et al. |
| 2007/0191344 | A1 | 8/2007 | Choidas et al. |
| 2009/0221581 | A1 | 9/2009 | Wabnitz et al. |
| 2010/0168144 | A1 | 7/2010 | Schauerte et al. |
| 2010/0184780 | A1 | 7/2010 | Schauerte et al. |
| 2010/0184789 | A1 | 7/2010 | Wabnitz et al. |

FOREIGN PATENT DOCUMENTS

| WO | 2005026129 A1 | 3/2005 |
| WO | 2006125616 A2 | 11/2006 |

OTHER PUBLICATIONS

Ulrich, Chapter 4: Crystallization, Kirk-Othmer Encyclopedia of Chemical Technology, pp. 1-7, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Gura et al., Systems for identifying new drugs are often faulty, Science, 278:1041-1042, 1997.*
Banker et al., Prodrugs, Modern Pharmaceutics, Third Edition, Revised and Expanded, pp. 451 and 596, 1996.*
Bundgaard, Design of Prodrugs, p. 1, 1985.*
Wolff, Some consideration for prodrug design, Burgers Medicinal Chemistry and Drug Discovery, 5th edition, vol. I: Principles and Practice, pp. 975-977, 1995.*
Traxler, Protein Tyrosine Kinase Inhibitors in cancer treatment, Expert Opinion on Therapeutic patents, 7(6):571-588, 1997.*
Simone, Oncology: Introduction, Cecil Textbook of Medicine, 20th Edition, vol. 1, pp. 1004-1010, 1996.*
LuValle et al., "Cell Cycle Control in Growth Plate Chondocytes", Frontiers in Bioscience 5, d493-503 (May 2000).*
Douglas, Jr., Introduction to Viral Diseases, Cecil Textbook of Medicine, 20th Edition, vol. 2, pp. 1739-1747, 1996.*
Blain et al., Different Integration of the Cyclin-dependent kinase (CDK) inhibitor p27Kipi with Cyclin A-Cdk2 and Cyclin D2-Cdk4, The Journal of Biological Chemistry, 272(41):25863-72 (1997).*
Damasio, Alzheimer's Disease and Related Dementias, Cecil Textbook of Medicine, 20th Edition, vol. 2, 1992-6, 1996.*
Layzer, Degenerative Diseases of the Nervous System, Cecil Textbook of Medicine, 20th Edition, vol. 2, 2050-7, 1996.*
Johnson et al., Relationships between drug activity in NCI preclinical in vitro and in vivo models and early clinical trials, British Journal of Cancer, 84(10):1424-1431, 2001.* S.R. Byrn et al., Solid State Chemistry of Drugs, 233-247, 516 (2nd Ed., 1999).
J.H. Poupaert, Drug Design: Basic Principles and Applications, 2 Encyclopedia of Pharmaceutical Technology, 1362-1369, 1367 (James Swarbrick ed., 3rd ed., 2007).
Chemotherapy of Neoplastic Diseases, Neoplastic Agents, Goodman & Gilman's: The Pharmacological Basis of Therapeutics, 1315-1403, 1315 (L.L. Brunton et al., eds., 11th ed. 2006).
Nonomura et al., "Gene Transfer of a Cell Cycle Modulator Exerts Anti-Inflammatory Effects in the Treatment of Arthritis" J. Immunol. Nov. 1, 2003; 171 (9) 4913-4919.

* cited by examiner

Primary Examiner — Deepak Rao
(74) Attorney, Agent, or Firm — Olson & Cepuritis, Ltd.

(57) ABSTRACT

The present invention provides new compounds. The compounds are useful as CDK5 inhibitors, and accordingly they can be included in pharmaceuticals compositions for treating any type of pain, inflammatory disorders, immunological diseases, proliferative diseases, infectious diseases, cardiovascular diseases and neurodegenerative diseases. formula (I).

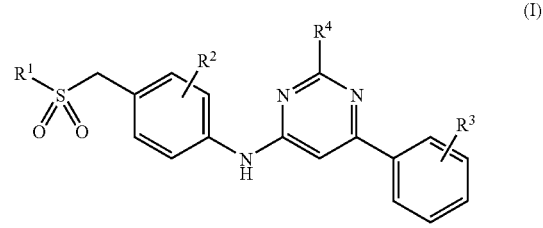

12 Claims, 1 Drawing Sheet

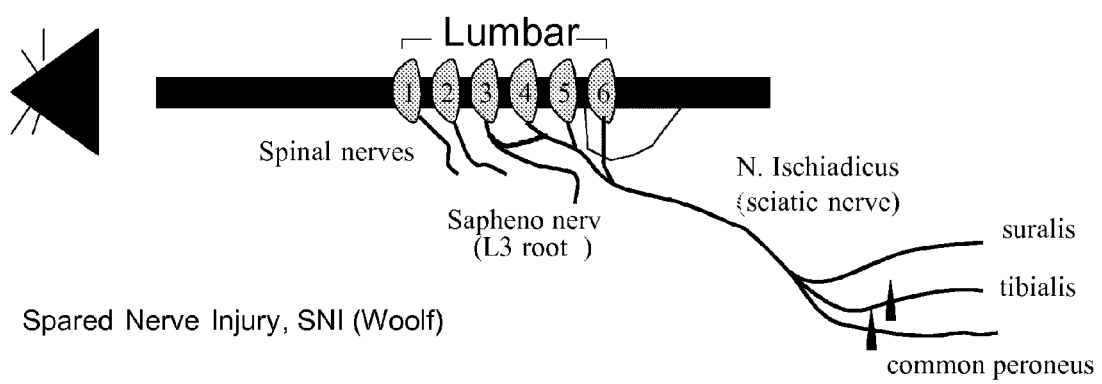

INHIBITORS OF PROTEIN KINASES

This application is the National Stage of PCT/EP2008/054972, filed on Apr. 24, 2008, which is incorporated herein by reference in its entirety.

BACKGROUND OF THE INVENTION

Cyclin-dependent protein kinases ("CDKs"), constitute a family of well-conserved enzymes that play multiple roles within the cell, such as cell cycle regulation and transcriptional control (Science 1996, Vol. 274:1643-1677; Ann. Rev. Cell Dev. Biol., 1997, 13:261-291).

Some members of the family, such as CDK1, 2, 3, 4, and 6 regulate the transition between different phases of the cell cycle, such as the progression from a quiescent stage in G1 (the gap between mitosis and the onset of DNA replication for a new round of cell division) to S (the period of active DNA synthesis), or the progression from G2 to M phase, in which active mitosis and cell division occur. Other members of this family of proteins, including CDK7, 8, and 9 regulate key points in the transcription cycle, whereas CDK5 plays a role in neuronal and secretory cell function.

CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

It is known that cell-cycle dysregulation, which is one of the cardinal characteristics of neoplastic cells, is closely associated with genetic alteration and deregulation of CDKs and their regulators, suggesting that inhibitors of CDKs may be useful as therapeutics for proliferative diseases, such as cancer. Thus, small molecule inhibitors targeting CDKs have been the focus of extensive interest in cancer therapy (Current Opinion in Pharmacology, 2003(3): 362-370). The ability of inhibiting cell cycle progression suggests a general role for small molecule inhibitors of CDKs as therapeutics for proliferative diseases, such as cancer. While inhibition of cell cycle-related CDKs is clearly relevant in oncology applications, this may not be the case for the inhibition of RNA polymerase-regulating CDKs.

The serine/threonine kinase CDK5 along with its cofactor p25 (or the longer cofactor, p35) has been linked to neurodegenerative disorders, and inhibitors of cdk5/p25 (or cdk5/p35) are therefore useful for the treatment of neurodegenerative disorders such as Alzheimer's disease, Parkinson's disease, stroke, or Huntington's disease. Treatment of such neurodegenerative disorders using CDK5 inhibitors is supported by the finding that CDK5 is involved in the phosphorylation of tau protein (J. Biochem, 117, 741-749 (1995)). CDK5 also phosphorylates Dopamine and Cyclic AMP-Regulated Phosphorprotein (DARPP-32) at threonine 75 and is thus indicated in having a role in dopaminergic neurotransmission (Nature, 402. 669-671 (1999)).

Cyclin-dependent kinase 5 (CDK5) is involved in regulating the state of phosphorylation of DARPP-32. CDK5 was originally identified as a homologue of p34$^{cdc2}$ protein kinase. Subsequent studies have shown that unlike cdc2, CDK5 kinase activity is not detected in dividing cells. Instead, the active form of CDK5 is present only in differentiated neurons, where it associates with a neuron-specific 35 kDa regulatory subunit, termed p35. CDK5/p35 plays a variety of roles in the developing and adult nervous system.

Recent studies have linked mis-regulation of CDK5 to Alzheimer's disease (Kusakawa, G. et al. 2000. J. Biol. Chem. 275:17166-17172; Lee, M. S. et al. 2000. Nature 405:360-364; Nath, R. et al. 2000. Biochem. Biophys. Res. Commun. 274:16-21; Patrick, G. N. et al. 1999. Nature 402:615-622). In these studies, conversion of p35 to p25 by the action of calpain causes prolonged activation and altered localization of CDK5. In turn, cdk5/p25 can hyperphosphorylate tau, disrupt cytoskeletal structure and promote apoptosis of primary neurons.

Recent studies have also shown that CDK5 phosphorylates DARPP-32 at Thr75 (Nishi, A. et al. 2000. Proc. Natl. Acad. Sci. USA 97:12840-12845; Bibb, J. A. et al. 1999. Nature 402:669-671). DARPP-32 phosphorylated at Thr75 is an inhibitor of PKA (Bibb et al. 1999. Nature 402:669-671). Phosphorylation of DARPP-32 at Thr75 by CDK5, by inhibiting PKA, decreases phosphorylation of Thr34 in DARPP-32 by PKA and plays an important modulatory role in the DARPP-32/PP1 cascade (Bibb, J. A. et al. 1999. Nature 402: 669-671).

Surprisingly little is known about the regulation of CDK5 by first messengers and other signalling events. Therefore, there is a need in the art to provide new compounds that can be used to develop novel compositions or drugs that can be used to treat diseases or disorders related to the regulation of CDK5. Furthermore, there is a need to develop treatments for such diseases or disorders that are due, at least in part, to an aberration or dysregulation of an intracellular signalling pathway regulated by CDK5. The present invention provides such methods and compositions.

Furthermore, the involvement of CDK5 in pain signalling has been reviewed in Pareek et al., PNAS 103, pp. 791-796, and in Pareek et al., Cell Cycle 5:6, pp. 585-588.

More than 50 pharmacological CDK inhibitors have been described, some of which have potent antitumor activity (Current Opinion in Pharmacology, 2003(3): 362-370). A comprehensive review about the known CDK inhibitors may be found in Angew. Chem. Int. Ed. Engl. 2003, 42(19):2122-2138.

The use of 2-anilino-4-phenylpyrimidine derivatives as cyclin-dependent kinase inhibitors for the treatment of e.g. cancer has been reported in WO 2005/012262. Furthermore, 2-pyridinylamino-4-thiazolyl-pyrimidine derivatives for the treatment of cancer etc. have been described in WO 2005/012298. The use of 4,5-dihydro-thiazolo, oxazolo and imidazolo[4,5-h]quinazolin-8-ylamines as protein kinase inhibitors is known from WO 2005/005438. Furthermore, indolinone derivatives and induribin derivatives, which are useful as cyclin-dependent kinase inhibitors have been disclosed in WO 02/081445 and WO 02/074742. Additionally, CDK inhibitors for various therapeutic applications have been described in WO2005/026129.

Known CDK inhibitors may be classified according to their ability to inhibit CDKs in general or according to their selectivity for a specific CDK. Flavopiridol, for example, acts as a "pan" CDK antagonist and is not particularly selective for a specific CDK (Current Opinion in Pharmacology, 2003(3): 362-370). Purine-based CDK inhibitors, such as olomoucine, roscovitine, purvanolols and CGP74514A are known to exhibit a greater selectivity for CDKs 1, 2 and 5, but show no inhibitory activity against CDKs 4 and 6 (Current Opinion in Pharmacology, 2003(3): 362-370). Furthermore, it has been demonstrated that purine-based CDK inhibitors such as roscovitine can exert anti-apoptotic effects in the nervous system (Pharmacol Ther 2002, 93:135-143) or prevent neuronal death in neurodegenerative diseases, such as Alzheimers's disease (Biochem Biophys Res Commun 2002 (297):1154-1158; Trends Pharmacol Sci 2002 (23):417-425).

Given the tremendous potential of targeting CDKs for the therapy of conditions such as proliferative, immunological, infectious, cardiovascular and neurodegenerative diseases, the development of small molecules as selective inhibitors of particular CDKs constitutes a desirable goal.

The present invention provides novel small molecule inhibitors of cyclin-dependent kinases. Preferably, said small molecule inhibitors show an increased potency to inhibit a particular CDK. Said small molecule inhibitors may have a therapeutic utility for the treatment of conditions such as proliferative, immunological, neurodegenerative, infectious and cardiovascular diseases. Furthermore, the small molecule inhibitors of the present invention have surprisingly been shown to exert a beneficial effect in the treatment of inflammatory diseases and of any type of pain.

Current treatments for pain are only partially effective, and many also cause debilitating or dangerous side effects. For example, many of the traditional analgesics used to treat severe pain induce debilitating side effects such as nausea, dizziness, constipation, respiratory depression, and cognitive dysfunction (Brower, 2000).

Although there is already a broad panel of approved pain medications like non-narcotic analgesics, opioid analgesics, calcium channel blockers, muscle relaxants, and systemic corticosteroids available, said treatments remain merely empirical and, while they may relieve the symptoms of pain, they do not lead to complete relief in most cases. This is also due to fact that the mechanisms underlying the development of the different types of pain are still only poorly understood. Researchers are only just beginning to appreciate the complexity and diversity of the signalling systems used to relay nerve impulses for each type of pain.

Generally, pain is defined as an unpleasant sensory and emotional experience associated with actual or potential tissue damage, or described in terms of such damage, according to the International Association for the Study of Pain (IASP). Specifically, pain may occur as acute or chronic pain.

Acute pain occurs for brief periods of time, typically less than 1 month and is associated with temporary disorders. It is a natural body response to let the host be aware of physiological or biochemical alteration that could result in further damage within a short period of time. It is felt when noxious stimuli activate high threshold mechanical and/or thermal nociceptors in peripheral nerve endings and the evoked action potentials in thinly myelinated (Aδ) and/or unmyelinated (C) afferent fibres reach a conscious brain. Said noxious stimuli may be provided by injury, surgery, illness, trauma or painful medical procedures. Acute pain usually disappears when the underlying cause has been treated or has healed. Unrelieved acute pain, however, may lead to chronic pain problems that may result in long hospital stays, rehospitalizations, visits to outpatient clinics and emergency departments, and increased health care costs.

In contrast to acute pain, chronic pain persists long after the initial injury has healed and often spreads to other parts of the body, with diverse pathological and psychiatric consequences. Chronic somatic pain results from inflammatory responses to trauma in peripheral tissues (e.g., nerve entrapment, surgical procedures, cancer, or arthritis), which leads to oversensitization of nociceptors and intense searing pain responses to normally non-noxious stimuli (hyperalgesia). Chronic pain is continuous and recurrent and its intensity will vary from mild to severe disabling pain that may significantly reduce quality of life.

Chronic pain is currently treated with conventional analgesics such as NSAIDs (Ibuprofen, Naproxen), Cox-2 inhibitors (Celecoxib, Valdecoxib, Rofecoxib) and opiates (codeine, morphine, thebain, papaverin, noscapin). For a significant number of patients however, these drugs provide insufficient pain relief.

Another subtype of pain, inflammatory pain, can occur as acute as well as chronic pain. Resulting injuries of tissue and neurons must not but may develop into long-lasting chronic neuropathic pain effects in succession to such inflammatory events.

Inflammatory pain is mediated by noxious stimuli like e.g. inflammatory mediators (e.g. cytokines, such as TNF α, prostaglandins, substance P, bradykinin, purines, histamine, and serotonine), which are released following tissue injury, disease, or inflammation and other noxious stimuli (e.g. thermal, mechanical, or chemical stimuli). In addition, cytokines and growth factors can influence neuronal phenotype and function (Besson 1999). These mediators are detected by nociceptors (sensory receptors) that are distributed throughout the periphery of the tissue. Said nociceptors are sensitive to noxious stimuli (e.g. mechanical, thermal, or chemical), which would damage tissue if prolonged (Koltzenburg 2000). A special class of so called C-nociceptors represent a class of "silent" nociceptors that do not respond to any level of mechanical or thermal stimuli but are activated in presence of inflammation only.

Current approaches for the treatment of especially inflammatory pain aim at cytokine inhibition (e.g. IL1β) and suppression of pro-inflammatory TNFα. Current approved anti-cytokine/antiTNFalpha treatments are based on chimeric antibodies such as Infliximab and Etanercept which reduce TNFα circulation in the bloodstream. TNFα is one of the most important inflammatory mediators that induces synthesis of important enzymes such as COX-2, MMP, iNOS, cPLa$_2$ and others. The main drawbacks of these "biologicals", however, reside in their immunogenic potential with attendant loss of efficacy and their kinetics that lead to a more or less digital all-or-nothing reduction of circulating TNFα. The latter can result in severe immune suppressive side effects.

A distinct form of chronic pain, neuropathic (or neurogenic) pain, arises as a result of peripheral or central nerve dysfunction and includes a variety of conditions that differ in etiology as well as location. Generally, the causes of neuropathic pain are diverse, but share the common symptom of damage to the peripheral nerves or components of central pathways. The causative factors might be metabolic, viral or mechanical nerve lesion. Neuropathic pain is believed to be sustained by aberrant somatosensory processes in the peripheral nervous system, the CNS, or both. Neuropathic pain is not directly linked to stimulation of nociceptors, but instead, is thought to arise e.g. from oversensitization of glutamate receptors on postsynaptic neurons in the gray matter (dorsal horn) of the spinal cord.

Neuropathic pain is associated with conditions such as nerve degeneration in diabetes and postherpetic neuralgia (shingles). Neuropathic pain conditions are the consequence of a number of diseases and conditions, including diabetes, AIDS, multiple sclerosis, stump and phantom pain after amputation, cancer-related neuropathy, post-herpetic neuralgia, traumatic nerve injury, ischemic neuropathy, nerve compression, stroke, spinal cord injury.

Management of neuropathic pain remains a major clinical challenge, partly due to an inadequate understanding of the mechanisms involved in the development and maintenance of neuropathic pain. Many existing analgesics are ineffective in treating neuropathic pain and most of current narcotic and non-narcotic drugs do not control the pain. Current clinical practice includes the use of a number of drug classes for the management of neuropathic pain, for example anticonvulsants, tricyclic antidepressants, and systemic local anaesthetics. However, the usual outcome of such treatment is partial or unsatisfactory pain relief, and in some cases the adverse effects of these drugs outweigh their clinical usefulness. Classic analgesics are widely believed to be poorly effective or ineffective in the treatment of neuropathic pain. Few clinical studies on the use of non steroidal anti-inflammatory drugs (NSAIDs) or opiates in the treatment of neuropathic pain have been conducted, but in those which have, the results appear to indicate that NSAIDs are poorly effective or ineffective and opiates only work at high doses. A review analysing the controlled clinical data for peripheral neuropathic pain (PNP) (Pain, November, 1997 73(2), 123-39) reported that NSAIDs were probably ineffective as analgesics for PNP and that there was no long-term data supporting the analgesic effectiveness of any drug.

Available analgesic drugs often produce insufficient pain relief. Although tricyclic antidepressants and some antiepileptic drugs, for example gabapentin, lamotrigine and carbamazepine, are efficient in some patients, there remains a large unmet need for efficient drugs for the treatment of these conditions.

In conclusion, there is a high unmet need for safe and effective methods of pain treatment, in particular of chronic inflammatory and neuropathic pain.

SUMMARY OF THE INVENTION

The present invention is directed to inhibitors of cyclin-dependent kinases and to methods and compositions for treating and/or preventing any type of pain, inflammatory disorders, immunological diseases, proliferative diseases, infectious diseases, cardiovascular diseases and neurodegenerative diseases comprising: administering an effective amount of at least one inhibitor of a cyclin-dependent kinase (cdk, CDK) to a subject in need thereof. The inhibitor is selected among compounds according to the general Formula I:

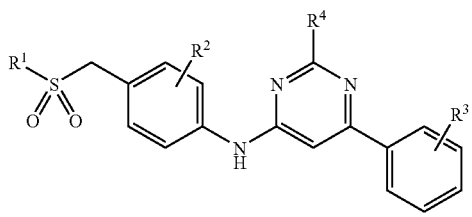

Formula I wherein
$R^1$ is chosen from the group of —$NR^5R^6$, —$R^8$, —$C_{1-4}$ alkyl-OH, or —$C_{2-4}$-alkylene—O—$C_{1-4}$ alkyl;
wherein
$R^5$ and $R^6$ independently of each other are hydrogen, $C_{1-4}$ alkyl, $C_{2-4}$ alkenyl, hydroxy-$C_{1-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkylene, $C_{4-7}$ aryl-$C_{0-4}$ alkylene, or $C_{4-7}$ heteroaryl-$C_{0-4}$ alkylene, or
wherein $R^5$ and $R^6$ together with the N-atom to which they are bound also may form a 5- to 8-membered heterocycloalkyl or a 5- to 6 membered heteroaryl,
wherein said cycloalkyl, heterocycloalkyl, aryl, heteroaryl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O— and —$NR^5R^6$;
$R^8$ is $C_{1-4}$ alkyl, $C_{2-4}$ alkenyl, hydroxy-$C_{2-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkyl;
X is $C_{1-4}$ alkylene including branched alkylene, preferably methylene, wherein said $C_{1-4}$ alkylene can be bound to $R^5R^6$, or $R^8$ to form a 5- to 6-membered heterocycle;
wherein said cycloalkyl, heterocycloalkyl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O and $NR^5R^6$;
$R^2$ can be from 0 to 2 substituents independently chosen from the group of halo;
$R^3$ can be 1 to 3 substituents independently selected from the group consisting of hydrogen, halo, hydroxy, $C_{1-4}$alkyl, $C_{3-7}$cycloalkyl, $C_{1-4}$ alkyl-cycloalkyl, $C_{1-4}$ alkyl-heterocycloalkyl, —O-heterocycloalkyl, $C_{1-4}$ alkoxy, $C_{1-4}$ alkenyloxy, —$OCF_3$, $C_{2-4}$ alkanoyl, $C_{1-4}$alkylsulfonyl, mono- and di-($C_1$-$C_4$alkyl)sulfonamido, aminocarbonyl, mono- and di-($C_1$-$C_4$alkyl)aminocarbonyl, aryl-$C_{1-4}$ alkoxy, heteroaryl-$C_{1-4}$ alkoxy, heterocycloalkyl-$C_{1-4}$ alkoxy, heterocycloalkyl-$C_{1-4}$ alkyl, heteroaryl-$C_{1-4}$-alkyl, $C_{1-4}$ alkyloxymethyl, hydroxy-$C_{1-4}$alkyloxymethyl, cyano, —COOH and $C_1$-$C_4$ alkoxycarbonyl, wherein the above mentioned substituents can be further substituted by radicals selected from the group of $C_{1-4}$-alkyl, hydroxyl-$C_{0-4}$-alkyl, $C_{1-4}$-alkoxy, aminocarbonyl, halo and $NR^5R^6$;
$R^4$ is selected from hydrogen, $C_{1-4}$ alkyl or —NR'R", wherein R' and R" each are independently selected from hydrogen, and $C_{1-4}$ alkyl;
and the N-oxide derivatives, prodrug derivatives, protected derivatives, individual isomers and mixtures of isomers thereof; and the pharmaceutically acceptable salts and solvates (e.g., hydrates) of such compounds.

As disclosed herein, the term "$C_{1-4}$ alkyl" is meant to include straight or branched chain saturated aliphatic hydrocarbon having 1 to 4 carbon atoms, such as methyl, ethyl, n-propyl, isopropyl, n-butyl, sec-butyl, isobutyl, tert-butyl. The term "lower alkenyl" refers to straight or branched chain alkene groups which have from 2 to 6 carbon atoms, such as, for example, vinyl, allyl, but-2-enyl, -but-3-enyl, or isopropenyl; the term "lower alkenyl" preferably represents allyl, -but-2-enyl, or but-3-enyl.

As disclosed herein, the term "halo" is meant to include fluoro-, chloro-, bromo-, and iodo-.

The term $C_3$-$C_8$ cycloalkyl denotes the following cycloalkyls:

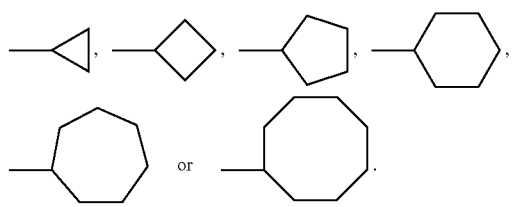

The term aryl denotes an aromatic mono- or bicyclic 6 to 10 membered ring system such as phenyl, naphthyl, 3-chlorophenyl, 2,6-dibromophenyl, 2,4,6 tribromophenyl, 4,7-dichloronaphthyl, and preferably phenyl or naphthyl.

The term heterocycloalkyl is meant to include a 5 to 10 membered mono- or bicyclic ring system, containing one to three heteroatoms independently selected from oxygen, sulfur or nitrogen and is preferably selected from the group comprising: pyrrolidinyl, tetrahydrofuranyl, piperidinyl, piperadizinyl, piperazinyl, tetrahydropyranyl, tetrahydrothiopyranyl or morpholinyl.

The term heterocyclyl further comprises all heteroaryls as defined below, wherein all double bonds of the correspondent heteroaryls are replaced by single bonds.

The term heteroaryl denotes a partially or fully unsaturated 5 to 10 membered mono- or bicyclic ringsystem, containing one to three heteroatoms independently selected from oxygen, sulfur or nitrogen and is preferably selected from the group consisting of:
Pyrrolyl, furanyl, thienyl, imidazolyl, pyrazolyl, thiazolyl, oxazolyl, isothiazolyl, isoxazolyl, pyridyl, pyrimidyl, pyrazyl, pyridazinyl, pyradizyl, 3-methylpyridyl, benzothienyl, 4-ethylbenzothienyl, 3,4-diethylfuranyl, pyrrolyl, tetrahydroquinolyl, quinolyl, tetrahydroisoquinolinyl, isoquinolinyl, benzoimidazolyl, benzothiazolyl, benzoxyzolyl, indolyl, benzofuranyl, benzothiophenyl, indazolyl.

It is to be understood, that the term heteroaryl also comprises partially unsaturated 5 to 10 membered mono- or bicyclic ringsystem, wherein one up to 4 double bonds of the ringsystem are replaced by a single bond and wherein the ringsystem contains at least one double bond.

When any variable occurs more than once in Formula I or in any substituent, its definition on each occurrence is independent of its definition at every other occurrence. For example, when a compound comprises more than one $R^5$ and/or $R^6$ substituent, these substituents can be the same or different.

It is preferred that the compounds have a structure according to the general Formula Ia:

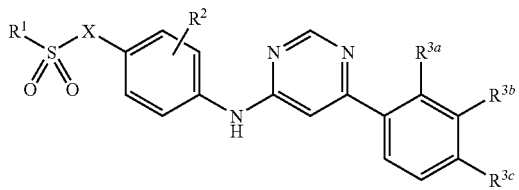

Formula Ia wherein
$R^{3a}$ is chosen from the group of hydrogen, $C_{1-4}$ alkoxy, $C_{2-4}$ alkenyloxy, aryl-$C_{1-4}$ alkoxy, and heteroaryl-$C_{1-4}$ alkoxy;
$R^{3b}$ is chosen from the group of hydrogen, $C_{1-4}$ alkoxy, $C_{2-4}$ alkenyloxy and $C_{0-4}$ alkylNR$^5$R$^6$;
$R^{3c}$ is chosen from the group of hydrogen and halo;
with the proviso that $R^{3a}$ and $R^{3b}$ cannot simultaneously be hydrogen;
and wherein $R^1$, $R^2$, $R^5$, $R^6$ and X have the same meaning as previously defined
and the N-oxide derivatives, prodrug derivatives, protected derivatives, individual isomers and mixtures of isomers thereof; and the pharmaceutically acceptable salts and solvates (e.g., hydrates) of such compounds.
Furthermore, it is especially preferred that $R^1$ is chosen from the group of NH$_2$—, N-methyl-, N-propyl-, N-isopropyl-, N-cyclopropyl-, N-cyclopentyl-, N,N-diethyl-,
X is methylene;
$R^2$ is hydrogen
$R^{3a}$ is chosen from the group of hydrogen, methoxy-, ethoxy-, isopropyloxy-, and benzyloxy-;
$R^{3b}$ is chosen from the group of hydrogen, methoxy-, 3-hydroxymethyl-piperidin-1-ylmethyl-, 3-diethylaminomethyl-, 3-piperidin-1-ylmethyl-, 3-morpholin-4-ylmethyl-, 4-methyl-piperazin-1-ylmethyl-, and [1,2,4]triazol-1-ylmethyl-;
$R^{3c}$ is hydrogen or halo;
with the proviso that $R^{3a}$ and $R^{3b}$ cannot simultaneously by hydrogen;
and the N-oxide derivatives, prodrug derivatives, protected derivatives, individual isomers and mixtures of isomers thereof; and the pharmaceutically acceptable salts and solvates (e.g., hydrates) of such compounds.

The following compounds are preferred:
C-{4-[6-(2-Ethoxy-phenyl)-pyrimidin-4-ylamino]-phenyl}-N-propyl-methanesulfonamide (Compound 1);
N-Cyclopentyl-C-{4-[6-(2-ethoxy-phenyl)-pyrimidin-4-ylamino]-phenyl}-methanesulfonamide (Compound 2);
C-{4-[6-(2-Benzyloxy-phenyl)-pyrimidin-4-ylamino]-phenyl}-N-cyclopentyl-methanesulfonamide (Compound 3);
C-{4-[6-(2-Benzyloxy-phenyl)-pyrimidin-4-ylamino]-phenyl}-N-isopropyl-methanesulfonamide (Compound 4);
C-{4-[6-(2-Benzyloxy-phenyl)-pyrimidin-4-ylamino]-phenyl}-N-cyclopropyl-methanesulfonamide (Compound 5);
{4-[6-(2-Ethoxy-phenyl)-pyrimidin-4-ylamino]-phenyl}-methanesulfonamide (Compound 6);
C-{4-[6-(2-Ethoxy-phenyl)-pyrimidin-4-ylamino]-phenyl}-N-methyl-methanesulfonamide (Compound 7);
{4-[6-(2-Benzyloxy-phenyl)-pyrimidin-4-ylamino]-phenyl}-methanesulfonamide (Compound 8);
{4-[6-(2,3-Dimethoxy-phenyl)-pyrimidin-4-ylamino]-phenyl}-methanesulfonamide (Compound 9);
N,N-Diethyl-C-{4-[6-(2-methoxy-phenyl)-pyrimidin-4-ylamino]-phenyl}-methanesulfonamide (Compound 10);
C-{4-[6-(2-Benzyloxy-phenyl)-pyrimidin-4-ylamino]-phenyl}-N-methyl-methanesulfonamide (Compound 11);
{4-[6-(3-Methoxy-phenyl)-pyrimidin-4-ylamino]-phenyl}-methanesulfonamide (Compound 12)
{4-[6-(2-Methoxy-phenyl)-pyrimidin-4-ylamino]-phenyl}-methanesulfonamide (Compound 13)
N-Cyclopentyl-C-{4-[6-(2-methoxy-phenyl)-pyrimidin-4-ylamino]-phenyl}-methanesulfonamide (Compound 14)
N-Cyclopentyl-C-{4-[6-(2-isopropoxy-phenyl)-pyrimidin-4-ylamino]-phenyl}-methanesulfonamide (Compound 15)
N-Cyclopentyl-C-{4-[6-(4-fluoro-2-methoxy-phenyl)-pyrimidin-4-ylamino]-phenyl}-methanesulfonamide (Compound 16)
(4-{6-[3-(3-Hydroxymethyl-piperidin-1-ylmethyl)-phenyl]-pyrimidin-4-ylamino}-phenyl)-methanesulfonamide (Compound 17)
{4-[6-(3-Diethylaminomethyl-phenyl)-pyrimidin-4-ylamino]-phenyl}-methanesulfonamide (Compound 18)
{4-[6-(3-Piperidin-1-ylmethyl-phenyl)-pyrimidin-4-ylamino]-phenyl}-methanesulfonamide (Compound 19)
{4-[6-(3-Morpholin-4-ylmethyl-phenyl)-pyrimidin-4-ylamino]-phenyl}-methanesulfonamide (Compound 20)
(4-{6-[3-(4-Methyl-piperazin-1-ylmethyl)-phenyl]-pyrimidin-4-ylamino}-phenyl)-methanesulfonamide (Compound 21)

{4-[6-(3-[1,2,4]Triazol-1-ylmethyl-phenyl)-pyrimidin-4-ylamino]-phenyl}-methanesulfonamide (Compound 22)

N-Cyclopentyl-C-(4-{6-[3-(3-hydroxymethyl-piperidin-1-ylmethyl)-phenyl]-pyrimidin-4-ylamino}-phenyl)-methanesulfonamide (Compound 23)

N-Cyclopentyl-C-{4-[6-(3-diethylaminomethyl-phenyl)-pyrimidin-4-ylamino]-phenyl}-methanesulfonamide (Compound 24)

N-Cyclopentyl-C-{4-[6-(3-piperidin-1-ylmethyl-phenyl)-pyrimidin-4-ylamino]-phenyl}-methanesulfonamide (Compound 25)

N-Cyclopentyl-C-{4-[6-(3-morpholin-4-ylmethyl-phenyl)-pyrimidin-4-ylamino]-phenyl}-methanesulfonamide (Compound 26)

N-Cyclopentyl-C-(4-{6-[3-(4-methyl-piperazin-1-ylmethyl)-phenyl]-pyrimidin-4-ylamino}-phenyl)-methanesulfonamide (Compound 27)

N-Cyclopentyl-C-{4-[6-(3-[1,2,4]triazol-1-ylmethyl-phenyl)-pyrimidin-4-ylamino]-phenyl}-methanesulfonamide (Compound 28)

In a further embodiment, the invention provides the above mentioned compounds according to Formula I, for medical use.

In a further embodiment, the invention provides pharmaceutical compositions containing a compound as outlined above, together with a pharmaceutically acceptable carrier.

In a further embodiment, the invention provides use of a compound as outlined above for preparing a pharmaceutical composition for treating inflammatory disorders, immunological diseases, proliferative diseases, infectious diseases, cardiovascular diseases and neurodegenerative diseases.

In a further embodiment, the invention provides use of a compound as outlined above for preparing a pharmaceutical composition for treating pain, chronic pain, and/or neuropathic pain.

In a further embodiment, the invention provides a method for treating inflammatory disorders, immunological diseases, proliferative diseases, infectious diseases, cardiovascular diseases and neurodegenerative diseases comprising the administration of an effective amount of at least one of the compounds as mentioned above to a subject in need thereof.

In a further embodiment, the invention provides a method for treating pain, chronic pain and/or neuropathic pain comprising the administration of an effective amount of at least one of the compounds as mentioned above to a subject in need thereof.

BRIEF DESCRIPTION OF THE DRAWINGS

FIG. 1 schematically depicts the spared nerve injury model (SNI model, as developed by Decosterd and Woolf (2000), which is characterized by ligation and section of two branches of the sciatic nerve (namely tibial and common peroneal nerves) leaving the sural nerve intact.

DETAILED DESCRIPTION OF THE PRESENT INVENTION

The inhibitors of CDK5 provided by the present invention are selected among compounds according to the general Formula I:

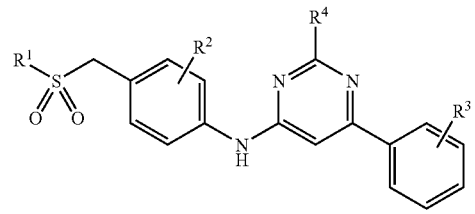

Formula I wherein
$R^1$ is chosen from the group of —$NR^5R^6$, —$R^8$, —$C_{1-4}$ alkyl-OH, or —$C_{2-4}$-alkylene-O—$C_{1-4}$ alkyl;
  wherein
  $R^5$ and $R^6$ independently of each other are hydrogen, $C_{1-4}$ alkyl, $C_{2-4}$ alkenyl, hydroxy-$C_{1-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkylene, $C_{4-7}$ aryl-$C_{0-4}$ alkylene, or $C_{4-7}$ heteroaryl-$C_{0-4}$ alkylene, or
  wherein $R^5$ and $R^6$ together with the N-atom to which they are bound also may form a 5- to 8-membered heterocycloalkyl or a 5- to 6 membered heteroaryl,
  wherein said cycloalkyl, heterocycloalkyl, aryl, heteroaryl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O— and —$NR^5R^6$;
  $R^8$ is $C_{1-4}$ alkyl, $C_{2-4}$ alkenyl, hydroxy-$C_{2-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkyl;
X is $C_{1-4}$ alkylene including branched alkylene, preferably methylene, wherein said $C_{1-4}$ alkylene can be bound to $R^5R^6$, or $R^8$ to form a 5- to 6-membered heterocycle;
  wherein said cycloalkyl, heterocycloalkyl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O and —$NR^5R^6$;
$R^2$ can be from 0 to 2 substituents independently chosen from the group of halo;
$R^3$ can be 1 to 3 substituents independently selected from the group consisting of hydrogen, halo, hydroxy, $C_{1-4}$alkyl, $C_{3-7}$cycloalkyl, $C_{1-4}$ alkyl-cycloalkyl, $C_{1-4}$ alkyl-heterocycloalkyl, —O-heterocycloalkyl, $C_{1-4}$ alkoxy, $C_{1-4}$ alkenyloxy, —$OCF_3$, $C_{2-4}$ alkanoyl, $C_{1-4}$alkylsulfonyl, mono- and di-($C_1$-$C_4$alkyl)sulfonamido, aminocarbonyl, mono- and di-($C_1$-$C_4$alkyl)aminocarbonyl, aryl-$C_{1-4}$ alkoxy, heteroaryl-$C_{1-4}$ alkoxy, heterocycloalkyl-$C_{1-4}$ alkoxy, heterocycloalkyl-$C_{1-4}$ alkyl, heteroaryl-$C_{1-4}$-alkyl, $C_{1-4}$ alkyloxymethyl, hydroxy-$C_{1-4}$alkyloxymethyl, cyano, —COOH and $C_1$-$C_4$ alkoxycarbonyl, wherein the above mentioned substituents can be further substituted by radicals selected from the group of $C_{1-4}$-alkyl, hydroxyl-$C_{0-4}$-alkyl, $C_{1-4}$-alkoxy, aminocarbonyl, halo and $NR^5R^6$;
$R^4$ is selected from hydrogen, $C_{1-4}$ alkyl or —NR'R", wherein R' and R" each are independently selected from hydrogen, and $C_{1-4}$ alkyl;
and the N-oxide derivatives, prodrug derivatives, protected derivatives, individual isomers and mixtures of isomers thereof; and the pharmaceutically acceptable salts and solvates (e.g., hydrates) of such compounds.

Particularly preferred compounds of the invention are those listed in Table I:

TABLE 1

| No | Compound | IUPAC name | MS m/z | Melt point ° C. |
|---|---|---|---|---|
| 1 | | C-{4-[6-(2-Ethoxy-phenyl)-pyrimidin-4-ylamino]-phenyl}-N-propyl-methanesulfonamide | 427 (M + 1) | 234.1-235.0 |
| 2 | | N-Cyclopentyl-C-{4-[6-(2-ethoxy-phenyl)-pyrimidin-4-ylamino]-phenyl}-methanesulfonamide | 453 (M + 1) | 189.0-190.0 |
| 3 | | C-{4-[6-(2-Benzyloxy-phenyl)-pyrimidin-4-ylamino]-phenyl}-N-cyclopentyl-methanesulfonamide | 515 (M + 1) | 210.1-211.0 |
| 4 | | C-{4-[6-(2-Benzyloxy-phenyl)-pyrimidin-4-ylamino]-phenyl}-N-isopropyl-methanesulfonamide | 489 (M + 1) | 168.8-169.5 |
| 5 | | C-{4-[6-(2-Benzyloxy-phenyl)-pyrimidin-4-ylamino]-phenyl}-N-cyclopropyl-methanesulfonamide | 487 (M + 1) | 178.0-178.8 |
| 6 | | {4-[6-(2-Ethoxy-phenyl)-pyrimidin-4-ylamino]-phenyl}-methanesulfonamide | 385 (M + 1) | 213.5-215.1 |
| 7 | | C-{4-[6-(2-Ethoxy-phenyl)-pyrimidin-4-ylamino]-phenyl}-N-methyl-methanesulfonamide | 399 (M + 1) | 218.0-219.0 |
| 8 | | {4-[6-(2-Benzyloxy-phenyl)-pyrimidin-4-ylamino]-phenyl}-methanesulfonamide | 447 (M + 1) | 213.7-215.9 |
| 9 | | {4-[6-(2,3-Dimethoxy-phenyl)-pyrimidin-4-ylamino]-phenyl}-methanesulfonamide | 401 (M + 1) | 247.8-250.5 |

TABLE 1-continued

| No | Compound | IUPAC name | MS m/z | Melt point ° C. |
|---|---|---|---|---|
| 10 | | N,N-Diethyl-C-{4-[6-(2-methoxy-phenyl)-pyrimidin-4-ylamino]-phenyl}-methanesulfonamide | 427 (M + 1) | 233.9-235.8 |
| 11 | | C-{4-[6-(2-Benzyloxy-phenyl)-pyrimidin-4-ylamino]-phenyl}-N-methyl-methanesulfonamide | 461 (M + 1) | amorphous, softening above 85° C. |
| 12 | | {4-[6-(3-Methoxy-phenyl)-pyrimidin-4-ylamino]-phenyl}-methanesulfonamide | 371, 372 (M + 1) | |
| 13 | | {4-[6-(2-Methoxy-phenyl)-pyrimidin-4-ylamino]-phenyl}-methanesulfonamide | 371, 373 (M + 1) | |
| 14 | | N-Cyclopentyl-C-{4-[6-(2-methoxy-phenyl)-pyrimidin-4-ylamino]-phenyl}-methanesulfonamide | 439 (M + 1) | 217.5-218.5 |
| 15 | | N-Cyclopentyl-C-{4-[6-(2-isopropoxy-phenyl)-pyrimidin-4-ylamino]-phenyl}-methanesulfonamide | 467 (M + 1) | 193.7-194.6 |
| 16 | | N-Cyclopentyl-C-{4-[6-(4-fluoro-2-methoxy-phenyl)-pyrimidin-4-ylamino]-phenyl}-methanesulfonamide | 456.83 (M + 1) | 260.5-261.5 |
| 17 | | (4-{6-[3-(3-Hydroxymethyl-piperidin-1-ylmethyl)-phenyl]-pyrimidin-4-ylamino}-phenyl)-methanesulfonamide | 468 (M + 1) | 224-226 |

TABLE 1-continued

| No | Compound | IUPAC name | MS m/z | Melt point ° C. |
|---|---|---|---|---|
| 18 | | {4-[6-(3-Diethylaminomethyl-phenyl)-pyrimidin-4-ylamino]-phenyl}-methanesulfonamide | 426 (M + 1) | 232 |
| 19 | | {4-[6-(3-Piperidin-1-ylmethyl-phenyl)-pyrimidin-4-ylamino]-phenyl}-methanesulfonamide | 438 (M + 1) | |
| 20 | | {4-[6-(3-Morpholin-4-ylmethyl-phenyl)-pyrimidin-4-ylamino]-phenyl}-methanesulfonamide | 440 (M + 1) | |
| 21 | | (4-{6-[3-(4-Methyl-piperazin-1-ylmethyl)-phenyl]-pyrimidin-4-ylamino}-phenyl)-methanesulfonamide | 453, 455 (M + 1) | |
| 22 | | {4-[6-(3-[1,2,4]Triazol-1-ylmethyl-phenyl)-pyrimidin-4-ylamino]-phenyl}-methanesulfonamide | 422, 444, 460 (M + 1) | |
| 23 | | N-Cyclopentyl-C-(4-{6-[3-(3-hydroxymethyl-piperidin-1-ylmethyl)-phenyl]-pyrimidin-4-ylamino}-phenyl)-methanesulfonamide | 536 (M + 1) | 218-219 |
| 24 | | N-Cyclopentyl-C-{4-[6-(3-diethylaminomethyl-phenyl)-pyrimidin-4-ylamino]-phenyl}-methanesulfonamide | 494 (M + 1) | |
| 25 | | N-Cyclopentyl-C-{4-[6-(3-piperidin-1-ylmethyl-phenyl)-pyrimidin-4-ylamino]-phenyl}-methanesulfonamide | 506 (M + 1) | 209-210 |
| 26 | | N-Cyclopentyl-C-{4-[6-(3-morpholin-4-ylmethyl-phenyl)-pyrimidin-4-ylamino]-phenyl}-methanesulfonamide | 508 (M + 1) | |

TABLE 1-continued

| No | Compound | IUPAC name | MS m/z | Melt point ° C. |
|----|----------|------------|--------|-----------------|
| 27 | | N-Cyclopentyl-C-(4-{6-[3-(4-methyl-piperazin-1-ylmethyl)-phenyl]-pyrimidin-4-ylamino}-phenyl)-methanesulfonamide | 521 (M + 1) | |
| 28 | | N-Cyclopentyl-C-{4-[6-(3-[1,2,4]triazol-1-ylmethyl-phenyl)-pyrimidin-4-ylamino]-phenyl}-methanesulfonamide | 490 (M + 1) | 224-226 |

The present invention thus provides new drugs or compounds, which drugs may be used in therapeutic methods for the treatment of a CDK5-related disorder.

The present invention also provides compositions containing these new drugs or compounds for modulating the activity of CDK5.

The present invention further provides methods for performing rational drug design to develop drugs that can modulate activity of CDK5 and thereby ameliorate a CDK5-related disorder.

The CDK5-inhibiting activity of a compound according to the present invention in a cell or tissue of interest can be determined by a method comprising: (a) determining a first level of cyclin-dependent kinase 5 activity in said cell or tissue; (b) contacting said cell or tissue with a test compound; and (c) determining a second level of cyclin-dependent kinase 5 activity in said cell or tissue, wherein a difference in said first level and said second level of cyclin-dependent kinase 5 activity is indicative of the ability of said test compound to modulate cyclin-dependent kinase 5 activity.

The present invention also provides diagnostic and therapeutic methods for the treatment of a CDK5-related disorder, including, but not limited the use of compositions or compounds of the invention in the treatment of a CDK5-related disorder.

The invention provides methods of administering an agent (or drug or compound) of the invention that can ameliorate a symptom of a CDK5-related disorder, disease and/or condition in a patient or subject exhibiting the symptom. In certain embodiments, the invention provides methods of administering an agent identified by the methods disclosed herein, that can ameliorate a symptom of a CDK5-related disorder in a patient or subject exhibiting the symptom.

As used herein, an "antagonist" is any compound that blocks the stimulation of a receptor and its resulting pharmacological effect.

As used herein, an "effective amount" of an inhibiting compound is an amount that can be determined by one of skill in the art based on data from studies using methods of analysis such as those disclosed herein.

As used herein, the terms "CDK5", "Cdk5" or "cdk5" are used interchangeably with "cyclin-dependent kinase 5," which is also known as neuronal cyclin-dependent-like protein (Nclk) and tau protein kinase II (TPKII). Cdk5 is a member of the cyclin dependent kinases but atypically Cdk5 employs a non-cyclin cofactor called neuronal cyclin-dependent-like kinase 5 associated protein (Nck5a) rather than a cyclin.

As used herein, the term "CDK5-related disorder" is used interchangeably with the terms "Cdk5 disorder," "Cdk5 condition," "Cdk5 dysfunction," "Cdk5-related dysfunction," "Cdk5-related disease," "Cdk5-related condition," "dysregulation of Cdk5 function" or "Cdk5 function dysregulation." A Cdk5-related disorder includes, but is not limited to, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, Huntington's Disease, Parkinson's disease, Tourette's syndrome, stroke, substance-induced psychotic disorder, for example psychosis induced by alcohol, amphetamine, cannabis, cocaine, hallucinogens, inhalants, opioids, or phencyclidine; personality disorder of the paranoid type; personality disorder of the schizoid type; drug addiction, including narcotic (e.g. heroin, opium, and morphine), cocaine and alcohol addiction; drug withdrawal, including narcotic, cocaine and alcohol withdrawal; epilepsy, sleep or circadian rhythm disorder (e.g., insomnia), sexual disorder, stress disorder, schizophrenia, attention deficit disorder (ADD), attention deficit hyperactivity disorder (ADHD), neurodegenerative disorder, substance or drug abuse, pain (Pareek et al., PNAS 103, pp. 791-796; Pareek et al., Cell Cycle 5:6, pp. 585-588), and cancer. A Cdk5-related disorder also includes, but is not limited to, a disease (e.g., depression) or a condition (e.g., addiction to cocaine) that involves an aberration or dysregulation of a signal transmission pathway, including but not limited to neurotransmission mediated by serotonergic receptors in excitable cells, tissues or organs (e.g., neurons, brain, central nervous system, etc.). A Cdk5-related disorder also includes, but is not limited to, a symptom of a Cdk5-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl Acad. Sci. USA 97:6809-68 14 (2000); and U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

Further diseases that are associated with abnormal cellular responses triggered by protein kinase-mediated events, such as CDK5-mediated events, include autoimmune diseases, inflammatory diseases, cardiovascular diseases, allergies and hormone-related diseases. In particular, kinases have been implicated in various diseases including: diabetes and mood disorders such as bipolar disorder; cardiomyocete hypertrophy; and development and regulation of sperm motility. Further, kineses been implicated in hair loss and neurotrauma, for example, stroke, traumatic brain surgery and spinal cord trauma. These diseases may be caused by, or result in, the abnormal operation of cell signalling pathways in which CDK5 plays a role. Accordingly, molecules that modulate the activity of kinase-mediated signaling are useful as therapeutic agents in the treatment of such diseases.

Further examples of diseases or conditions where a kinase, such as CDK5 may play a role include cancer. The cancer may be a carcinoma, for example carcinoma of the bladder, breast, colon, kidney, liver, lung, for example small cell lung cancer, esophagus, gall bladder, ovary, pancreas, stomach, cervix, thyroid, prostate, or skin, for example squamous cell carcinoma; a hematopoietic tumor of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukemias, myelodyplastic syndrome, or promyelocytic leukemia; a tumor of mesenchymal origin, for example fibrosarcoma or rhabdomyosarcoma; a tumor of the central or peripheral nervous system, for example astrocytoma, neuroblastomas, glioma or schwannoma; melanoma; seminoma; teratocarcinoma; osteosarcoma; xenoderoma pigmentoum; keratoctanthoma; thyroid follicular cancer; or Kaposi's sarcoma. Diseases or conditions comprising benign abnormal cell growth include benign prostate hyperplasia, familial adenomatosis polyposis, neuro-fibromatosis, atherosclerosis, pulmonary fibrosis, arthritis, psoriasis, glomerulonephritis, restenosis, hypertrophic scar formation, inflammatory bowel disease, transplantation rejection, fungal infection, and endotoxic shock.

Pain

It has turned out that administration of CDK inhibitors according to Formula I have a hypoalgesic effect.

Thus, in a preferred embodiment, this invention relates to a method of treating any type of pain comprising administering an effective amount of an inhibitor of CDK5 according to Formula I. Specifically, the compounds of Formula I may be used for the treatment of chronic, neuropathic and/or inflammatory pain. In a particular preferred embodiment, the compounds of Formula I for use in the treatment of any type of pain display an increased selectivity for CDK5 than for other CDKs.

The role of CDK5 in the development of pain has been described in Pareek et al., PNAS 103, pp. 791-796 and in Pareek et al., Cell Cycle 5:6, pp. 585-588.

The term "pain" as used herein generally relates to any type of pain and broadly encompasses types of pain such as acute pain, chronic pain, inflammatory and neuropathic pain. In a preferred embodiment of the present invention, "pain" comprises neuropathic pain and associated conditions. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain.

Acute pain types comprise, but are not limited to pain associated with tissue damage, postoperative pain, pain after trauma, pain caused by burns, pain caused by local or systemic infection, visceral pain associated with diseases comprising: pancreatitis, intestinal cystitis, dysmenorrhea, Irritable Bowel syndrome, Crohn's disease, ureteral colic and myocardial infarction Furthermore, the term "pain" comprises pain associated with CNS disorders comprising: multiple sclerosis, spinal cord injury, traumatic brain injury, Parkinson's disease and stroke In a preferred embodiment, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto.

Inflammatory pain (pain in response to tissue injury and the resulting inflammatory process) as defined herein relates to inflammatory pain associated with diseases comprising connective tissue diseases, rheumatoid arthritis, systemic lupus erythematosus, multiple sclerosis and arthritis, but is not limited thereto.

Neuropathic pain (pain resulting from damage to the peripheral nerves or to the central nervous system itself) includes conditions comprising, but not limited to metabolic neuropathies (e.g., diabetic neuropathy), post-herpetic neuralgia, trigeminal neuralgia, cranial neuralgia, post-stroke neuropathic pain, multiple sclerosis-associated neuropathic pain, HIV/AIDS-associated neuropathic pain, cancer-associated neuropathic pain, carpal tunnel-associated neuropathic pain, spinal cord injury-associated neuropathic pain, complex regional pain syndrome, fibromyalgia-associated neuropathic pain, reflex sympathic dystrophy, phantom limb syndrome or peripheral nerve or spinal cord trauma, nerve transection including surgery, limb amputation and stump pain, pain caused by the side effects of anti-cancer and anti-AIDS therapies, post-surgical neuropathic pain, neuropathy-associated pain such as in idiopathic or post-traumatic neuropathy and mononeuritis, and neuropathic pain caused by connective tissue disease such as rheumatoid arthritis, Wallenberg's syndrome, systemic lupus erythematosus, multiple sclerosis, or polyarteritis nodosa. The neuropathy can be classified as radiculopathy, mononeuropathy, mononeuropathy multiplex, polyneuropathy or plexopathy.

The term "allodynia" denotes pain arising from stimuli which are not normally painful.

Allodynic pain may occur other than in the area stimulated.

The term "hyperalgesia" denotes an increased sensitivity to a painful stimulus.

The term "hypoalgesia" denotes a decrease of sensitivity to a painful stimulus.

Inflammatory Diseases

Surprisingly, it could be shown that the CDK inhibitors according to Formula I as disclosed herein exert an anti-inflammatory effect in in vitro and in vivo inflammatory assays.

Thus, in a preferred embodiment, this invention relates to a method of treating inflammatory diseases comprising administering an effective amount of an inhibitor of cyclin-dependent kinase according to Formula I. In a particular preferred embodiment, the compounds of Formula I for use in the treatment of inflammatory diseases display an increased selectivity for CDK5 than for other CDKs.

Thus, the compounds according to Formula I as presented herein may be used for the treatment and/or prevention of inflammatory diseases.

The term "inflammatory diseases" as used herein relates to diseases triggered by cellular or non-cellular mediators of the immune system or tissues causing the inflammation of body tissues and subsequently producing an acute or chronic inflammatory condition.

Examples of inflammatory diseases are hypersensitivity reactions of type I-IV, for example but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, Wegener's granulomatosis, glomerulonephritis, acute or chronic host versus graft reactions, dry eye disease, and severe dry eye disease resulting from Sjögren's syndrome.

Furthermore, the term "inflammatory diseases" includes but is not limited to abdominal cavity inflammation, dermatitis, gastrointestinal inflammation (including inflammatory bowel disease, ulcerative colitis), fibrosis, ocular and orbital inflammation, mastitis, otitis, mouth inflammation, musculoskeletal system inflammation (including gout, osteoarthritis), inflammatory diseases of the central nervous system (including multiple sclerosis, bacterial meningitis, meningitis), genitourinary tract inflammation (incl. prostatitis, glomerulonephritis), cardiovascular inflammation (including atherosclerosis, heart failure), respiratory tract inflammation (including chronic bronchitis, chronic obstructive pulmonary disease), thyroiditis, diabetes mellitus, osteitis, myositis, multiple organ failure (including. sepsis), polymyositis and psoriatic arthritis.

Immunological Diseases

The compounds according to Formula I are also envisaged to be useful in the treatment and/or prevention of immunological diseases, such as, for example, autoimmune diseases.

Accordingly, the present invention provides a method for the treatment and/or prevention of immunological diseases comprising the administration of an effective amount of at least one CDK5 inhibitor according to Formula I to a subject in need thereof.

The term "immunological diseases" as used herein relates to diseases including but not limited to allergy, asthma, graft-versus-host disease, immune deficiencies and autoimmune diseases.

Specifically, immunological diseases include diabetes, rheumatic diseases, AIDS, chronic granulomatosis disease, rejection of transplanted organs and tissues, rhinitis, chronic obstructive pulmonary diseases, osteoporosis, ulcerative colitis, Crohn's disease, sinusitis, lupus erythematosus, psoriasis, multiple sclerosis, myasthenia gravis, alopecia, recurrent infections, atopic dermatitis, eczema and severe anaphylactic reactions, but are not limited thereto. Furthermore, "immunological diseases" also include allergies such as contact allergies, food allergies or drug allergies.

Proliferative Diseases

The compounds of Formula I are inhibitors of cyclin-dependent kinases, which represent key molecules involved in regulation of the cell cycle. Cell-cycle disregulation is one of the cardinal characteristics of neoplastic cells. Thus, said compounds are expected to prove useful in arresting or recovering control of the cell cycle in abnormally dividing cells. It is thus expected that the compounds according to Formula I are useful in the treatment and/or prevention of proliferative diseases such as cancer.

Accordingly, the invention provides a method for the treatment and/or prevention of proliferative diseases comprising administering an effective amount of at least one inhibitor of a cyclin-dependent kinase according to Formula I.

As used herein, the term "proliferative disease" relates to cancer disorders, including, but not limited to benign neoplasms, dysplasias, hyperplasias as well as neoplasms showing metastatic growth or any other transformations.

The term "cancer" includes but is not limited to benign and malign neoplasia like carcinoma, sarcoma, carcinosarcoma, cancers of the blood-forming tissues, tumors of nerve tissues including the brain and cancer of skin cells.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, esophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronicmyelogenous leukemias, myelodysplastic syndrome, or promyelocytic leukemia; thyroid follicular cancer; a tumour of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; Kaposi's sarcoma, astrocytoma, basal cell carcinoma, small intestine cancer, small intestinal tumors, gastrointestinal tumors, glioblastomas, liposarcoma, germ cell tumor, head and neck tumors (tumors of the ear, nose and throat area), cancer of the mouth, throat, larynx, and the esophagus, cancer of the bone and its supportive and connective tissues like malignant or benign bone tumour, e.g. malignant osteogenic sarcoma, benign osteoma, cartilage tumors; like malignant chondrosarcoma or benign chondroma, osteosarcomas; tumors of the urinary bladder and the internal and external organs and structures of the urogenital system of male and female, soft tissue tumors, soft tissue sarcoma, Wilm's tumor or cancers of the endocrine and exocrine glands like e.g. thyroid, parathyroid, pituitary, adrenal glands, salivary glands.

Cardiovascular Diseases

Furthermore, the invention relates to the treatment and/or prevention of cardiovascular diseases comprising administering an effective amount of at least one inhibitor of a cyclin-dependent kinase according to Formula I.

It has been reported that the field of cariodvascular diseases constitutes a possible clinical application for CDK inhibitors (Pharmacol Ther 1999, 82(2-3):279-284).

Thus, in a preferred embodiment, the invention relates to a method of treating and/or preventing cardiovascular diseases comprising administering an effective amount of at least one inhibitor of a cyclin-dependent kinase according to Formula I, wherein said compound displays an increased selectivity for CDK5 than for other CDKs.

The term "cardiovascular diseases" includes but is not limited to disorders of the heart and the vascular system like congestive heart failure, myocardial infarction, ischemic diseases of the heart, such as stable angina, unstable angina and asymptomatic ischemia, all kinds of atrial and ventricular arrhythmias, hypertensive vascular diseases, peripheral vascular diseases, coronary heart disease and atherosclerosis. Furthermore, as used herein, the term includes, but is not limited to adult congenital heart disease, aneurysm, angina pectoris, angioneurotic edema, aortic valve stenosis, aortic aneurysm, aortic regurgitation, arrhythmogenic right ventricular dysplasia, arteriovenous malformations, atrial fibrillation, Behcet syndrome, bradycardia, cardiomegaly, cardiomyopathies such as congestive, hypertrophic and restrictive cardiomyopathy, carotid stenosis, cerebral hemorrhage, Churg-Strauss syndrome, cholesterol embolism, bacterial endocarditis, fibromuscular dysplasia, congestive heart failure, heart valve diseases such as incompetent valves or stenosed valves, heart attack, epidural or subdural hematoma, von Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, mitral valve prolapse, long QT syndrome mitral valve prolapse, myocardial ischemia, myocarditis, disorders of the pericardium, pericarditis, peripheral vascular diseases, phlebitis, polyarteritis nodosa, pulmonary atresia, Raynaud disease, restenosis, rheumatic heart disease, Sneddon syndrome, stenosis, superior vena cava syndrome, syndrome X, tachycardia, hereditary hemorrhagic telangiectasia, telangiectasis, temporal arteritis, thromboangiitis obliterans, thrombosis, thromboembolism, varicose veins, vascular diseases, vasculitis, vasospasm, ventricular fibrillation, Williams syndrome, peripheral vascular disease, varicose veins and leg ulcers, deep vein thrombosis and Wolff-Parkinson-White syndrome.

Furthermore, the term cardiovascular diseases includes diseases resulting from congenital defects, genetic defects, environmental influences (i.e., dietary influences, lifestyle, stress, etc.), and other defects or influences.

Neurodegenerative Diseases

CDK inhibitors have been described to exert neuroprotective effects. Specifically, it has been reported that CDK inhibitors prevent neuronal death in neurodegenerative diseases such as Alzheimer's disease (Biochem Biophys Res Commun 2002 (297):1154-1158; Trends Pharmacol Sci 2002 (23):417-425; Pharmacol Ther 1999, 82(2-3):279-284).

Thus, the compounds according to Formula I, which are CDK5 inhibitors, are expected to provide beneficial effects in the therapeutic management of neurodegenerative diseases.

Accordingly, the invention relates a method of treating and/or preventing neurodegenerative diseases comprising administering an effective amount of at least one inhibitor of a cyclin-dependent kinase according to Formula I.

The term "neurodegenerative diseases" as used herein includes disorders of the central nervous system as well as disorders of the peripheral nervous system, including, but not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease, dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, Korsakoff's psychosis and AIDS-related dementia.

Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be neurodegenerative disorders.

Specifically, the present invention relates to a method for treating the above-referenced types of pain and associated conditions and inflammatory disorders, immunological diseases, proliferative diseases, infectious diseases, cardiovascular diseases and neurodegenerative diseases, wherein the term "treating" comprises the prevention, amelioration or treating of pain and associated conditions and inflammatory disorders, immunological diseases, proliferative diseases, infectious diseases, cardiovascular diseases and neurodegenerative diseases Pharmaceutical Compositions Preferred embodiments of the present invention include the administration of compositions comprising at least one cyclin-dependent kinase inhibitor according to Formula I as an active ingredient together with at least one pharmaceutically acceptable (i.e. non-toxic) carrier, excipient and/or diluent.

Preferably, the composition comprises at least one cyclin-dependent kinase inhibitor according to Formula I as an active ingredient, wherein said at least one cyclin-dependent kinase inhibitor has an increased selectivity for CDK5 than for other CDKs.

Furthermore, the invention also comprises compositions combining at least two inhibitors of CDK and/or pharmaceutically acceptable salts thereof. Said at least two inhibitors may inhibit the same cyclin-dependent kinase or may also inhibit different types of cylin-dependent kinases, e.g. one inhibitor in the composition may inhibit CDK5 while the other inhibitor is capable of inhibiting CDK2, for example. However, one of the inhibitors is always a CDK5 inhibitor.

Having regard to pain treatment, an individual pain medication often provides only partially effective pain alleviation because it interferes with just one pain-transducing pathway out of many. Thus, it is also intended to administer CDK inhibitors according to Formula I in combination with a pain-reducing (analgesic) agent that acts at a different point in the pain perception process.

An "analgesic agent" comprises a molecule or combination of molecules that causes a reduction in pain perception. An analgesic agent employs a mechanism of action other than inhibition of CDK.

One class of analgesics, such as nonsteroidal anti-inflammatory drugs (NSAIDs), down-regulates the chemical messengers of the stimuli that are detected by the nociceptors and another class of drugs, such as opioids, alters the processing of nociceptive information in the CNS. Other analgesics are local anesthetics, anticonvulsants and antidepressants such as tricyclic antidepressants. Administering one or more classes of drug in addition to CDK inhibitors can provide more effective amelioration of pain.

Preferred NSAIDs for use in the methods and compositions of the present invention are aspirin, acetaminophen, ibuprofen, and indomethacin. Furthermore, cyclooxygenase-2 (COX-2) inhibitors, such as specific COX-2 inhibitors (e.g. celecoxib, COX189, and rofecoxib) may also be used as an analgesic agent in the methods or compositions of the present invention.

Preferred tricyclic antidepressants are selected from the group consisting of Clomipramine, Amoxapine, Nortriptyline, Amitriptyline, Imipramine, Desipramine, Doxepin, Trimipramine, Protriptylin, and Imipramine pamoate.

Furthermore, the use of anticonvulsants (e.g. gabapentin), GABAB agonists (e.g. L-baclofen), opioids, vanniloid receptor antagonists and cannabinoid (CB) receptor agonists, e.g.

CB1 receptor agonists as analgesic is also preferred in the methods and compositions in the present invention.

In preparing cyclin-dependent kinase inhibitor compositions of this invention, one can follow the standard recommendations of well-known pharmaceutical sources such as Remington: The Science and Practice of Pharmacy, $19^{th}$ ed. (Mack Publishing, 1995).

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, wherein said preparations in addition to typical vehicles and/or diluents contain at least one inhibitor according to the present invention and/or a pharmaceutical acceptable salt thereof as active ingredient.

The pharmaceutical compositions according to the present invention containing at least one inhibitor according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like.

Moreover, suitable binders, lubricants, disintegrating agents and coloring agents may also be incorporated into the tablet or capsule. Powders and tablets may contain about 5 to about 95% by weight of a cyclin-dependent kinase inhibitor according to the Formula I as recited herein or analogues thereof or the respective pharmaceutical active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like.

Suitable disintegrants include starch, methylcellulose, guar gum, and the like.

Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect (s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended or relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75% by weight, and more preferably from about 30 to about 60% by weight.

The term disintegrants refers to materials added to the composition to support disintegration and release of the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium-croscaramellose, alginates such as alginic acid and sodium alginate, clays such as bentonites, and effervescent mixtures. The amount of disintegrant in the composition may range from about 2 to about 20% by weight of the composition, more preferably from about 5 to about 10% by weight.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium or calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20% by weight of the composition, preferably from about 3 to about 10% by weight, and more preferably from about 3 to about 6% by weight.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5% by weight of the composition, preferably from about 0.5 to about 2% by weight, and more preferably from about 0.3 to about 1.5% by weight of the composition.

Glidents are materials that prevent baking of the components of the pharmaceutical composition together and improve the flow characteristics of granulate so that flow is smooth and uniform. Suitable glidents include silicon dioxide and talc.

The amount of glident in the composition may range from about 0.1 to about 5% by weight of the final composition, preferably from about 0.5 to about 2% by weight.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5% by weight of the composition, preferably from about 0.1 to about 1% by weight.

The present invention relates to the administration of compositions containing as active ingredient a cyclin-dependent kinase inhibitor to a subject in need thereof for the treatment of any type of pain, inflammatory disorders, immunological diseases, proliferative diseases, cardiovascular diseases or neurodegenerative diseases.

"A subject in need thereof" comprises an animal, preferably a mammal, and most preferably a human, expected to experience any type of pain, inflammatory disorders, immunological diseases, proliferative diseases, cardiovascular diseases or neurodegenerative diseases in the near future or which has ongoing experience of said conditions. For example, such animal or human may have a ongoing condition that is causing pain currently and is likely to continue to cause pain, or the animal or human has been, is or will be enduring a procedure or event that usually has painful consequences. Chronic painful conditions such as diabetic neuropathic hyperalgesia and collagen vascular diseases are examples of the first type; dental work, particularly in an area of inflammation or nerve damage, and toxin exposure (including exposure to chemotherapeutic agents) are examples of the latter type.

In order to achieve the desired therapeutic effect, the respective cyclin-dependent kinase inhibitor has to be administered in a therapeutically effective amount.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated. In the context of the present invention, a therapeutically effective amount comprises, e.g., an amount that reduces pain, in particular inflammatory or neuropathic pain. Specifically, a therapeutically effective amount denotes an amount which exerts a hypoalgesic effect in the subject to be treated.

Such effective amount will vary from subject to subject depending on the subject's normal sensitivity to, e.g., pain, its height, weight, age, and health, the source of the pain, the mode of administering the inhibitor of CDKs, the particular inhibitor administered, and other factors. As a result, it is advisable to empirically determine an effective amount for a particular subject under a particular set of circumstances.

The invention is further illustrated by the following non-limiting examples.

EXAMPLES

All reagents were purchased from ACROS Organics, Aldrich, Lancaster, Maybridge and Boron Molecular.

The LC/MS analyses for the compounds were done at Surveyor MSQ (Thermo Finnigan, USA) with APCI ionization.

The $^1$H NMR spectra were recorded on <<MERCURY plus 400 MHz>> spectrometer (Varian). Chemical shift values are given in ppm relative to tetramethylsilane (TMS), with the residual solvent proton resonance as internal standard.

Melting points were determined on Sanyo Gallenkamp apparatus.

Reference Example 1 (not According to Present Invention)

Synthesis of C-{3-[6-(2-methoxy-phenyl)-pyrimidin-4-ylamino]-phenyl}-N,N-dimethyl-methanesulfonamide (Reference Compound 1)

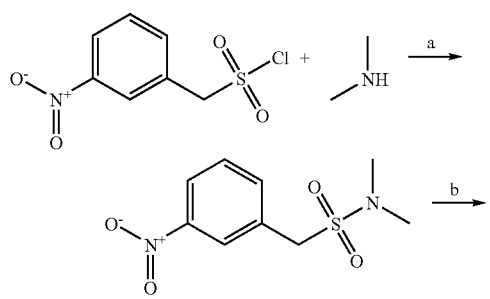

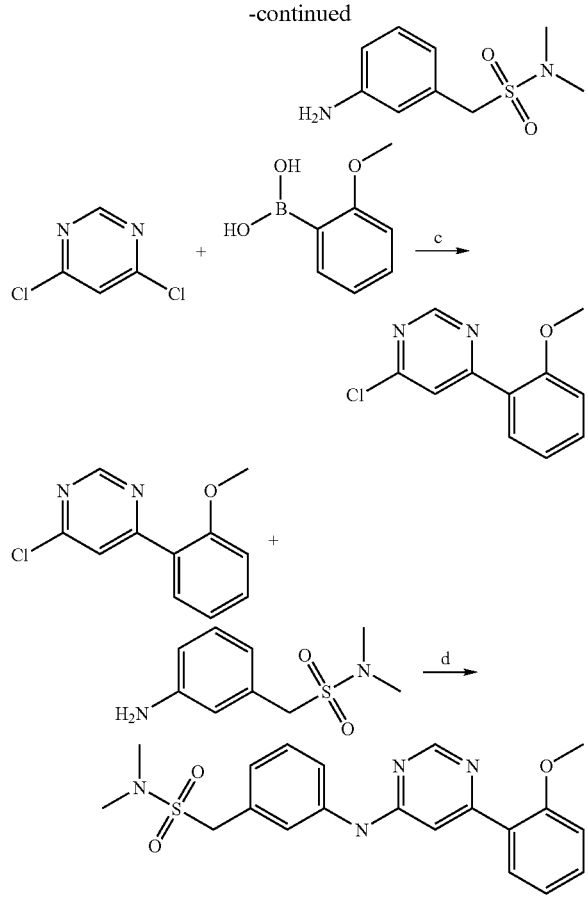

a. Synthesis of (3-nitrophenyl)-N,N-dimethylmethanesulfonamide (3-Nitrophenyl)methanesulfonyl chloride (2.36 g, 10 mmol) was dissolved in benzene (30 mL), then to this solution was added 40% aqueous dimethylamine (12.6 mL, 0.1 mol) and the reaction mixture was vigorously stirred for 2 h at room temperature. The benzene layer was separated and the aqueous layer extracted with $CH_2Cl_2$ (2×25 mL). The recombined oganic layers were washed with saturated aqueous $NaHCO_3$ (30 mL), water (30 mL) and the solvent removed under reduced pressure to give 2.32 g (95%) of (3-nitrophenyl)-N,N-dimethylmethanesulfonamide as crystals.

b. Synthesis of (3-aminophenyl)-N,N-dimethylmethanesulfonamide (3-Nitrophenyl)-N,N-dimethylmethanesulfonamide (2.32 g, 9.5 mmol) was hydrogenated over Raney nickel (0.5 g) in methanol at 50° C. and 70 psi for 4 h, then catalyst was filtered off, washed with warm methanol, combined filtrates were evaporated to give 1.95 g (96%) of (3-aminophenyl)-N,N-dimethylmethanesulfonamide.

c. Synthesis of 4-chloro-6-(2-methoxyphenyl)-pyrimidine

To a solution of 4,6-dichloropyrimidine (6.0 g, 40 mmol) and 2-methoxyphenylboronic acid (4.41 g, 29 mmol) in mixture of dimethoxyethane (120 mL) and water (18 mL) were added $NaHCO_3$ (6.72 g, 80 mmol) and $(PPh_3)_2PdCl_2$ (0.84 g) and the reaction mixture was refluxed for 8 h, and concentrated under reduced pressure. The resulting residue was taken up in $CH_2Cl_2$ (100 mL) and the solution washed with water, dried over anhydrous $K_2CO_3$, filtered and the solvent removed under reduced pressure. The obtained crude product was purified by flash chropatography on silica (eluent $CH_2Cl_2$) and recrystallized from hexanes. Yield of 4-chloro-6-(2-methoxyphenyl)-pyrimidine 4.78 g (75%).

d. Synthesis of C-{3-[6-(2-methoxy-phenyl)-pyrimidin-4-ylamino]-phenyl}-N,N-dimethyl-methanesulfonamide (Reference Compound 1)

A mixture of (3-aminophenyl)-N,N-dimethylmethanesulfonamide (0.107 g, 0.50 mmol) and 4-chloro-6-(2-methoxyphenyl)-pyrimidine (0.110 g, 0.10 mmol) in DMFA (3 mL) was stirred at 80° C. till the reaction completion (TLC control), then concentrated in vacuo and the residue was recrystallized from isopropanol to give C-{3-[6-(2-methoxyphenyl)-pyrimidin-4-ylamino]-phenyl}-N,N-dimethyl-methanesulfonamide (Reference compound 1)

Yield: 0.101 g (51%).

Melting point 187.5-188.8° C.

$^1$H-NMR (400 MHz, DMSO-$d_6$); δ (ppm) 2.76 (6H, s), 3.90 (3H, s), 4.40 (2H, s), 7.05-7.12 (2H, m), 7.18 (1H, d), 7.35 (1H, d), 7.42-7.49 (7H, m), 7.72 (1H, s), 7.77 (1H, d), 7.95 (1H, d), 8.70 (1H, s), 9.63 (1H, br. s).

CI MS m/z 399 (MH+)

Reference Example 2 (not According to Present Invention)

Synthesis of C-{3-[6-(2-benzyloxy-phenyl)-pyrimidin-4-ylamino]-phenyl}-N-propyl-methanesulfonamide (Reference Compound 2)

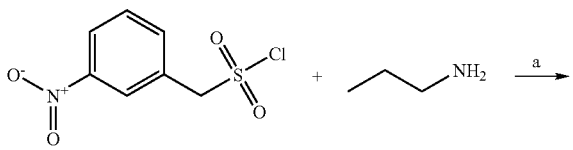

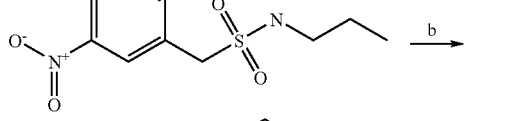

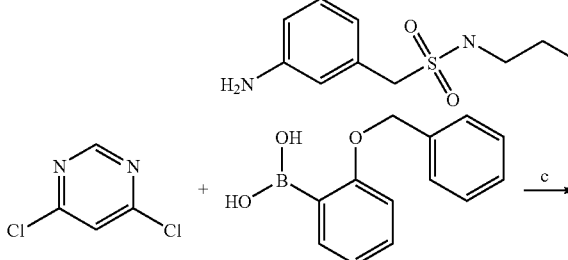

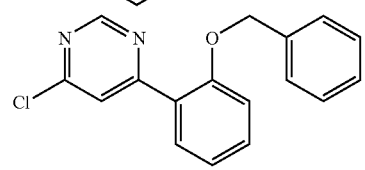

-continued

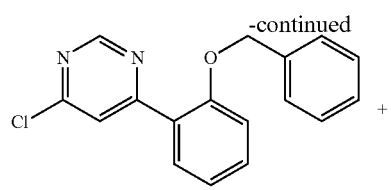

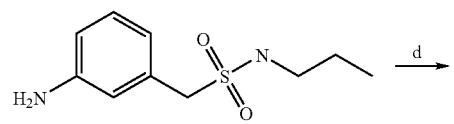

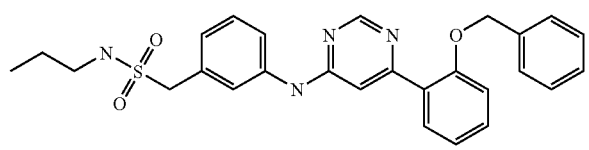

a. Synthesis of (3-nitrophenyl)-N-propylmethar le (3-Nitrophenyl)methanesulfonyl chloride (0.6 g, 2.55 mmol) was dissolved in acetonitrile (10 mL), then to this solution was added propylamine (0.247 ml, 3 mmol) and triethylamine (1 mL) and the reaction mixture was vigorously stirred for 3 h at room temperature. The obtained mixture was diluted with cold water (30 ml), which led to the formation of a precipitate that was filtered off, washed with water (2×10 mL) and dried.

Yield of (3-nitrophenyl)-N-propylmethanesulfonamide 0.63 g (95%).

b. Synthesis of (3-aminophenyl)-N-propylmethanesulfonamide

The same procedure as for Reference compound 1.

c. Synthesis of 4-chloro-6-(2-benzyloxyphenyl)-pyrimidine

The same procedure as for Reference compound 1.

d. Synthesis of C-{3-[6-(2-benzyloxy-phenyl)-pyrimidin-4-ylamino]-phenyl}-N-propyl-methanesulfonamide (Reference Compound 2)

The same procedure as for Reference compound 1.
Yield: 0.193 g (79%).
Melting point 114.7-116.0° C.
$^1$H-NMR (400 MHz, CDCl$_3$); δ (ppm) 0.90 (3H, t), 1.45-1.60 (2H, m), 3.01 (2H, q), 4.15 (2H, s), 5.15 (2H, s), 6.81 (1H, br. s), 7.03-7.46 (14H, m), 8.00 (1H, d), 8.79 (1H, s).
CI MS m/z 489 (MH+)

Example 1

Synthesis of C-{4-[6-(2-ethoxy-phenyl)-pyrimidin-4-ylamino]-phenyl}-N-propyl-methanesulfonamide (Compound 1)

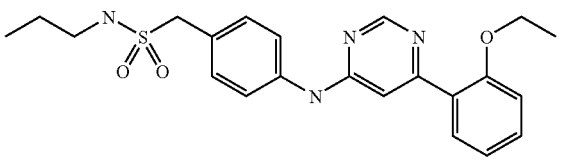 [SMILES: CCCNS(=O)(=O)Cc1ccc(Nc2cc(-c3ccccc3OCC)ncn2)cc1]

a. Synthesis of (4-nitrophenyl)-N-propylmethanesulfonamide

The same procedure as for Reference compound 2.

b. Synthesis of (4-aminophenyl)-N-propylmethanesulfonamide

The same procedure as for Reference compound 1.

c. Synthesis of 4-chloro-6-(2-ethoxyphenyl)-pyrimidine

The same procedure as for Reference compound 1.

d. Synthesis of C-{4-[6-(2-ethoxy-phenyl)-pyrimidin-4-ylamino]-phenyl}-N-propyl-methanesulfonamide (Compound 1).

The same procedure as for Reference compound 2.
Yield: 0.115 g (54%).
Melting point 234.1-235.0.
$^1$H-NMR (400 MHz, DMSO-d$_6$); δ (ppm) 0.83 (3H, t), 1.37 (3H, t), 1.43 (2H, tq), 2.86 (2H, q), 4.15 (2H, q), 4.25 (2H, s), 6.92 (1H, t), 7.05 (1H, t), 7.14 (1H, d), 7.33 (2H, d), 7.41 (1H, t), 7.47 (1H, s), 7.65 (2H, d), 7.93 (1H, d), 8.68 (1H, s9), 9.56 (1H, s).
CI MS m/z 427 (MH+)

Example 2

Synthesis of C-{4-[6-(2-ethoxy-phenyl)-pyrimidin-4-ylamino]-phenyl}-N-cyclopentyl-methanesulfonamide (Compound 2)

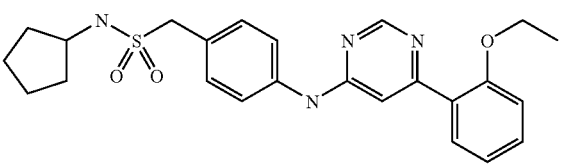 [SMILES: CCOc1ccccc1-c1cc(Nc2ccc(CS(=O)(=O)NC3CCCC3)cc2)ncn1]

a. Synthesis of (4-nitrophenyl)-N-cyclopentylmethanesulfonamide

The same procedure as for Reference compound 2.

b. Synthesis of (4-aminophenyl)-N-cyclopentylmethanesulfonamide

The same procedure as for Reference compound 1.

c. Synthesis of 4-chloro-6-(2-ethoxyphenyl)-pyrimidine

The same procedure as for Reference compound 1.

d. Synthesis of C-{4-[6-(2-ethoxy-phenyl)-pyrimidin-4-ylamino]-phenyl}-N-cyclopentyl-methanesulfonamide (Compound 2)

The same procedure as for Reference compound 1.
Yield: 0.165 g (73%).
Melting point 189.0-190.0° C.
$^1$H-NMR (400 MHz, DMSO-$d_6$); δ (ppm) 1.35-1.50 (7H, m), 1.52-1.68 (2H, m), 1.75-1.88 (2H, m), 3.56 (1H, m), 4.17 (2H, q), 4.27 (2H, s), 6.97 (1H, d), 7.06 (1H, t), 7.16 (1H, d), 7.35 (2H, d), 7.43 (2H, s), 7.64 (2H, d), 7.88 (1H, d), 8.71 (1H, s), 9.78 (1H, br. s).
CI MS m/z 453 (MH+)

Example 3

Synthesis of C-{4-[6-(2-benzyloxy-phenyl)-pyrimidin-4-ylamino]-phenyl}-N-cyclopentyl-methanesulfonamide (Compound 3)

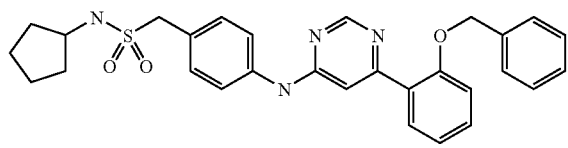 [SMILES: O=S(=O)(Cc1ccc(Nc2cc(-c3ccccc3OCc3ccccc3)ncn2)cc1)NC1CCCC1]

a. Synthesis of (4-nitrophenyl)-N-cyclopentylmethanesulfonamide

The same procedure as for Reference compound 2.

b. Synthesis of (4-aminophenyl)-N-cyclopentylmethanesulfonamide

The same procedure as for Reference compound 1.

c. Synthesis of 4-chloro-6-(2-benzyloxyphenyl)-pyrimidine

The same procedure as for Reference compound 2.

d. Synthesis of C-{4-[6-(2-benzyloxy-phenyl)-pyrimidin-4-ylamino]-phenyl}-N-cyclopentyl-methanesulfonamide (Compound 3)

The same procedure as for Reference compound 1.
Yield: 0.140 g (55%).
Melting point 210.1-211.0° C.
$^1$H-NMR (400 MHz, DMSO-$d_6$); δ (ppm) 1.35-1.50 (4H, m), 1.52-1.68 (2H, m), 1.73-1.88 (2H, m), 3.56 (1H, m), 4.23 (2H, s), 5.26 (2H, s), 6.96 (1H, d), 7.08 (1H, t), 7.21 (1H, d), 7.25-7.48 (9H, m), 7.63 (2H, d), 7.84 (1H, d), 8.70 (1H, s), 9.57 (1H, s)
CI MS m/z 515 (MH+).

Example 4

Synthesis of C-{4-[6-(2-benzyloxy-phenyl)-pyrimidin-4-ylamino]-phenyl}-N-isopropyl-methanesulfonamide (Compound 4)

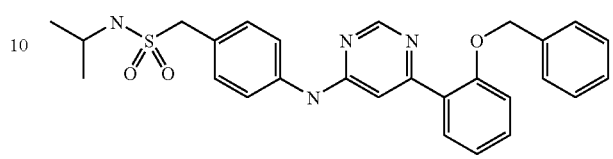

a. Synthesis of (4-nitrophenyl)-N-isopropylmethanesulfonamide

The same procedure as for Reference compound 2.

b. Synthesis of (4-aminophenyl)-N-isopropylmethanesulfonamide

The same procedure as for Reference compound 1.

c. Synthesis of 4-chloro-6-(2-benzyloxyphenyl)-pyrimidine

The same procedure as for Reference compound 1.

d. Synthesis of C-{4-[6-(2-benzyloxy-phenyl)-pyrimidin-4-ylamino]-phenyl}-N-isopropyl-methanesulfonamide (Compound 4)

The same procedure as for Reference compound 1.
Yield: 0.131 g (54%).
Melting point 168.8-169.5° C.
$^1$H-NMR (400 MHz, DMSO-$d_6$); δ (ppm) 1.10 (6H, d), 3.32-3.45 (1H, m), 4.23 (2H, s), 5.27 (2H, s), 6.85 (1H, d), 7.08 (1H, t), 7.21 (1H, d), 7.25-7.47 (9H, m), 7.63 (2H, d), 7.84 (1H, d), 8.70 (1H, s), 9.56 (1H, s).
CI MS m/z 489 (MH+)

Example 5

Synthesis of C-{4-[6-(2-benzyloxy-phenyl)-pyrimidin-4-ylamino]-phenyl}-N-cyclopropyl-methanesulfonamide (Compound 5)

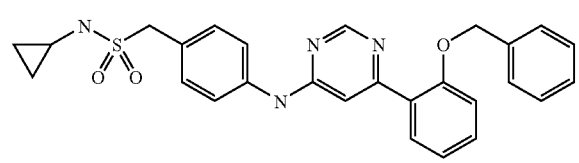 [SMILES: O=S(=O)(Cc1ccc(Nc2cc(-c3ccccc3OCc3ccccc3)ncn2)cc1)NC1CC1]

a. Synthesis of (4-nitrophenyl)-N-cyclopropylmethanesulfonamide

The same procedure as for Reference compound 2.

b. Synthesis of (4-aminophenyl)-N-cyclopropylmethanesulfonamide

The same procedure as for Reference compound 1.

c. Synthesis of 4-chloro-6-(2-benzyloxyphenyl)-pyrimidine

The same procedure as for Reference compound 1.

d. Synthesis of C-{4-[6-(2-benzyloxy-phenyl)-pyrimidin-4-ylamino]-phenyl}-N-cyclopropyl-methanesulfonamide (Compound 5)

The same procedure as for Reference compound 1.
Yield: 0.129 g (53%).
Melting point 178.0-178.8° C.
$^1$H-NMR (400 MHz, DMSO-$d_6$); δ (ppm) 0.50-0.65 (4H, m), 1.12-1.22 (1H, m), 4.30 (2H, s), 5.28 (2H, s), 7.08 (1H, t), 7.21 (1H, d), 7.25-7.47 (10H, m), 7.64 (2H, d), 7.84 (1H, d), 8.70 (1H, s), 9.57 (1H, s).
CI MS m/z 487 (MH+)

TABLE 2

Reference Examples 1-2 and Examples 1-5: Yields of the intermediates

| (3-nitrophenyl)methanesulfonamide | Yield % | (3-aminophenyl)methanesulfonamide | Yield % | 4-chloro-6-aryl-pyrimidine | Yield % |
|---|---|---|---|---|---|
| structure | 95 | structure | 95 | structure | 70 |
| structure | 95 | structure | 95 | structure | 73 |
| structure | 95 | structure | 96 | structure | 43 |
| structure | 95 | structure | 95 | structure | 42 |
| structure | 95 | structure | 95 | | |
| structure | 95 | | | | |

TABLE 2-continued

Reference Examples 1-2 and Examples 1-5: Yields of the intermediates

| (3-nitrophenyl)methanesulfonamide | Yield % | (3-aminophenyl)methanesulfonamide | Yield % | 4-chloro-6-aryl-pyrimidine | Yield % |
|---|---|---|---|---|---|
| 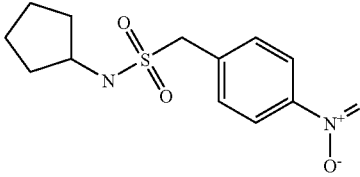 | 95 | | | | |

Reference Example 3 (not According to Present Invention)

Synthesis of C-{3-[6-(2-methoxy-phenyl)-pyrimidin-4-ylamino]-phenyl}-N-(3-methoxy-propyl)-methanesulfonamide (Reference Compound 3)

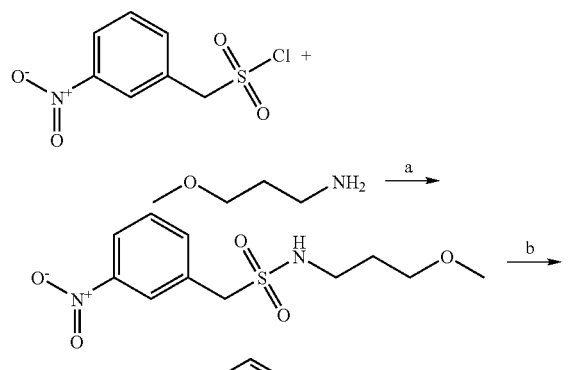

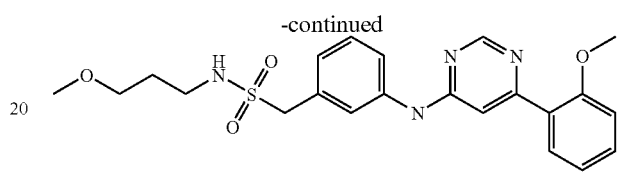

a. Synthesis of N-(3-methoxy-propyl)-C-(3-nitro-phenyl)-methanesulfonamide 3-metoxypropylamine (0.184 mL, 1.80 mmol) and triethylamine (0.3 mL) were added to a solution of (3-Nitrophenyl)methanesulfonyl chloride (0.35 g, 1.50 mmol) in acetonitrile (10 mL). The resulting solution was vigorously stirred for 3 h at room temperature and then diluted with cold water (30 ml), which lead to the formation of a precipitate. The precipitate was filtered off, washed with water (2×10 mL) and dried. Yield of N-(3-methoxy-propyl)-C-(3-nitro-phenyl)-methanesulfonamide 0.31 g (72%).

b. Synthesis of C-(3-amino-phenyl)-N-(3-methoxy-propyl)-methanesulfonamide

N-(3-Methoxy-propyl)-C-(3-nitro-phenyl)-methanesulfonamide (0.31 g, 1.08 mmol) was hydrogenated over Raney nickel (0.05 g) in methanol at 50° C. and 70 psi for 4 h. Then, the catalyst was filtered off, washed with warm methanol, and the combined filtrates were evaporated to give 0.14 g (50%) of C-(3-amino-phenyl)-N-(3-methoxy-propyl)-methanesulfonamide c. Synthesis of 4-chloro-6-(2-methoxyphenyl)-pyrimidine 4,6-dichloropyrimidine (6.0 g, 40 mmol) and 2-methoxyphenylboronic acid (4.41 g, 29 mmol) were added to a solution of dimethoxyethane (120 mL) and water (18 mL), followed by the addition of $NaHCO_3$ (6.72 g, 80 mmol) and $(PPh_3)_2PdCl_2$ (0.84 g). to this end the reaction mixture was allowed to reflux for 8 h, and then the solvent removed under reduced pressure. The residue was taken up in $CH_2Cl_2$ (100 mL), and the resulting solution washed with water, dried over anhydrous $K_2CO_3$, filtered and the solvent removed under reduced pressure. The crude product was purified by flash chropatography on silica gel (eluent $CH_2Cl_2$) and recrystallized from hexanes yielding 4-chloro-6-(2-methoxyphenyl)-pyrimidine (4.78 g; 75%).

d. Synthesis of C-{3-[6-(2-methoxy-phenyl)-pyrimidin-4-ylamino]-phenyl}-N-(3-methoxy-propyl)-methanesulfonamide (Reference Compound 3)

A mixture of C-(3-amino-phenyl)-N-(3-methoxy-propyl)-methanesulfonamide (0.129 g, 0.50 mmol) and 4-chloro-6-(2-methoxyphenyl)-pyrimidine (0.110 g, 0.10 mmol) in DMFA (3 mL) was stirred at 80° C. till the reaction completion (TLC control), then evaporated in vacuo. The resulting residue was purified by column chromatography on silica gel yielding C-{3-[6-(2-methoxy-phenyl)-pyrimidin-4-ylamino]-phenyl}-N-(3-methoxy-propyl)-methanesulfonamide Yield: 0.140 g (63%).

Melting point: 149.2-150.8° C.

$^1$H-NMR (400 MHz, DMSO-$d_6$); δ (ppm) 1.63 (2H, quint), 2.96 (2H, dt), 3.18 (3H, s), 3.33 (2H, t), 3.89 (3H, s), 4.28 (2H, s), 6.95-7.10 (3H, m), 7.17 (1H, d), 7.33 (1H, t), 7.40-7.48 (2H, m), 7.67 (1H, s), 7.77 (1H, d), 7.94 (1H, d), 8.67 (1H, s), 9.61 (1H, br. s).

CI MS m/z 443 (MH+)

Reference Example 4

Synthesis of C-{3-[6-(2-ethoxy-phenyl)-pyrimidin-4-ylamino]-phenyl}-N-methyl-methanesulfonamide (Reference compound 4)

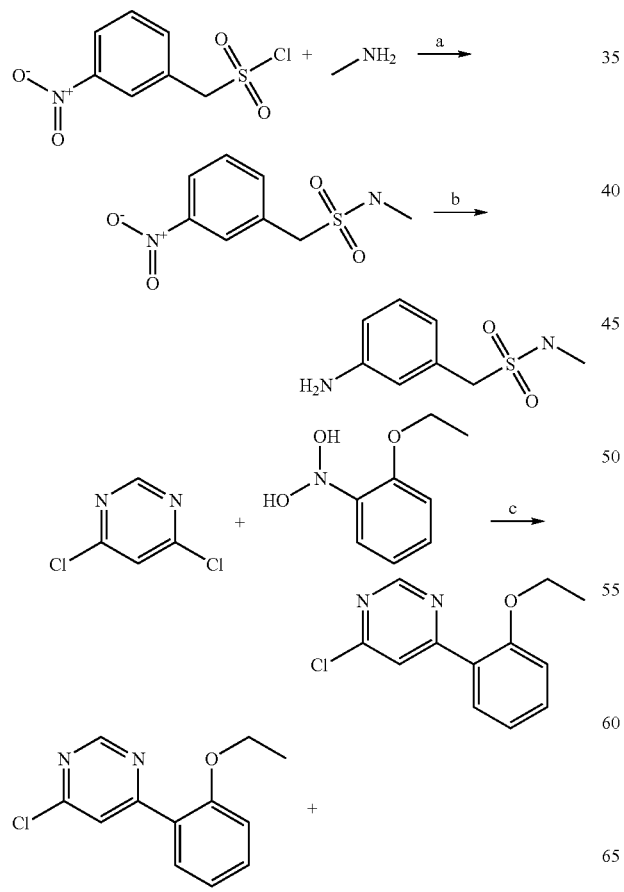

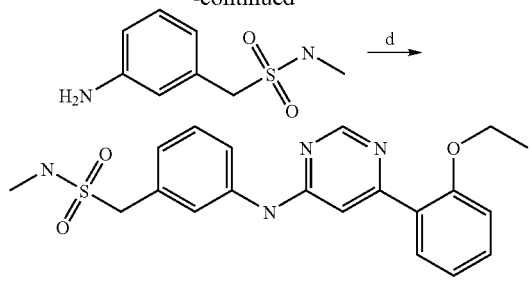

a. Synthesis of (3-nitrophenyl)-N-methylmethanesulfonamide

40% aqueous methylamine (10 mL, 0.1 mol) was added to a vigorously stirred solution of (3-nitrophenyl)methanesulfonyl chloride (2.36 g, 10 mmol) in benzene (30 mL) and allowed to stir for 2 h at room temperature. The benzene layer was separated, and the aqueous layer extracted with $CH_2Cl_2$ (2×25 mL). The combined organic layers were washed with saturated aqueous $NaHCO_3$ (30 mL), water (30 mL), filtered over anhydrous $Na_2SO_4$, filtered and the solvent removed under reduced pressure to give 2.07 g (90%) of (3-nitrophenyl)-N-methylmethanesulfonamide as crystals.

b. Synthesis of (3-aminophenyl)-N-methylmethanesulfonamide

The same procedure as for Reference compound 3.

c. Synthesis of 4-chloro-6-(2-ethoxyphenyl)-pyrimidine

The same procedure as for Reference compound 3.

d. Synthesis of C-{3-[6-(2-ethoxy-phenyl)-pyrimidin-4-ylamino]-phenyl}-N-methyl-methanesulfonamide (Reference compound 4)

The same procedure as for Reference compound 3.

Yield: 0.209 g (76%).

Melting point: 155.9-156.5° C.

$^1$H-NMR (400 MHz, DMSO-$d_6$); δ (ppm) 1.37 (3H, t), 2.58 (3H, d), 4.12 (2H, quart), 4.28 (2H, s), 6.83 (1H, br. quart), 7.04 (2H, t), 7.12 (1H, d), 7.32 (1H, t), 7.39 (1H, t), 7.46 (1H, s), 7.60 (1H, s), 7.77 (1H, d), 7.92 (1H, d), 8.67 (1H, s), 9.56 (1H, br. s).

CI MS m/z 399 (MH+)

Example 6

Synthesis of {4-[6-(2-ethoxy-phenyl)-pyrimidin-4-ylamino]-phenyl}-methanesulfonamide (Compound 6)

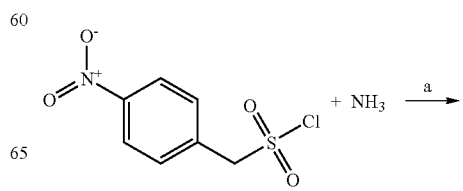

-continued

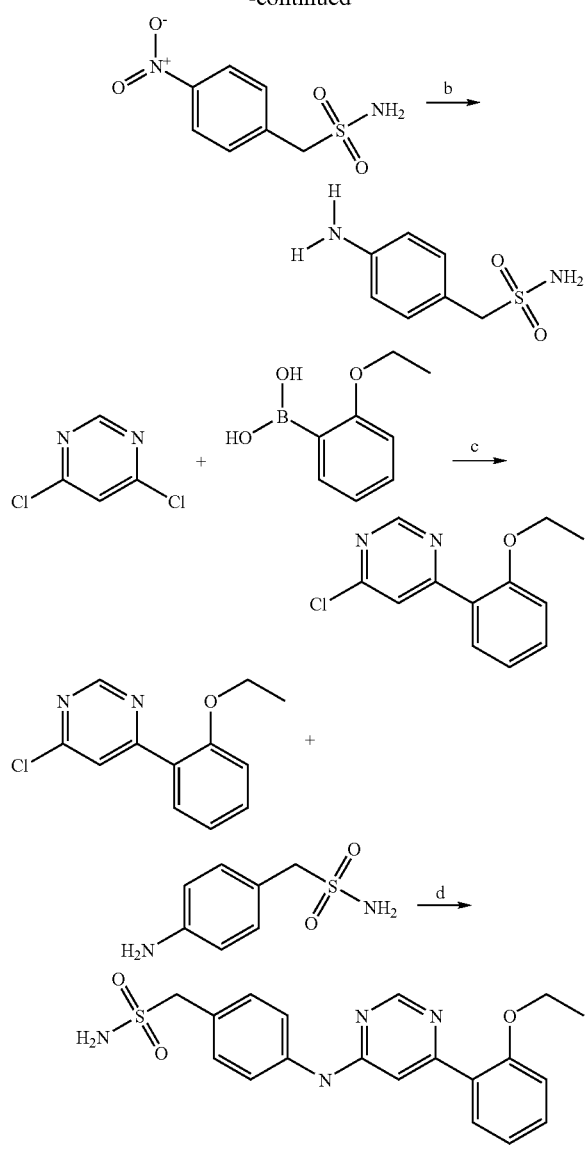

a. Synthesis of (4-nitrophenyl)methanesulfonyl amide (4-Nitrophenyl)methanesulfonyl chloride (1.0 g, 4.3 mmol) was dissolved in acetonitrile (10 mL), then to this solution was added concentrated aqueous ammonia (10 mL) saturated with ammonium carbonate and the reaction mixture was vigorously stirred for 1 h at room temperature. Then acetonitrile was removed under reduced pressure and the residue diluted with cold water (10 mL) leading to a precipitate formation. The precipitate was filtered off and washed with water (2×5 mL), ether and dried. Yield of (4-nitrophenyl)methanesulfonyl amide 0.6 g (65%)

b. Synthesis of (4-aminophenyl)methanesulfonyl amide

The same procedure as for Reference compound 3.

c. Synthesis of 4-chloro-6-(2-ethoxyphenyl)-pyrimidine

The same procedure as for Reference compound 3.

d. Synthesis of {4-[6-(2-ethoxy-phenyl)-pyrimidin-4-ylamino]-phenyl}-methanesulfonamide (Compound 6)

A mixture of (4-aminophenyl)methanesulfonyl amide (0.093 g, 0.50 mmol) and 4-chloro-6-(2-ethoxyphenyl)-pyrimidine (0.117 g, 0.50 mmol) in DMFA (3 mL) was stirred at 80° C. till the reaction completion (TLC control). Then the reaction mixture was concentrated in vacuo and the residue recrystallized from isopropanol to give {4-[6-(2-ethoxy-phenyl)-pyrimidin-4-ylamino]-phenyl}-methanesulfonamide (Compound 6)

Yield: 0.140 g (73%).
Melting point: 213.5-215.1° C.
$^{1}$H-NMR (400 MHz, DMSO-$d_6$); δ (ppm) 1.37 (3H, t), 4.13 (2H, q), 4.20 (2H, s), 6.70 (2H, br. s), 7.03 (1H, t), 7.13 (1H, d), 7.31 (2H, d), 7.39 (1H, t), 7.46 (1H, s), 7.64 (2H, d), 7.92 (1H, d), 8.66 (1H, s), 9.55 (1H, br. s).
CI MS m/z 385 (MH+)

Example 7

Synthesis of C-{4-[6-(2-ethoxy-phenyl)-pyrimidin-4-ylamino]-phenyl}-N-methyl-methanesulfonamide (Compound 7)

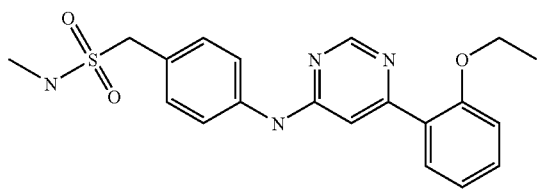 [SMILES: CCOc1ccccc1-c1cc(Nc2ccc(CS(=O)(=O)NC)cc2)ncn1]

a. Synthesis of (4-nitrophenyl)-N-methylmethanesulfonamide

The same procedure as for Reference compound 4.

b. Synthesis of (4-aminophenyl)-N-methylmethanesulfonamide

The same procedure as for Reference compound 3.

c. Synthesis of 4-chloro-6-(2-ethoxyphenyl)-pyrimidine

The same procedure as for Reference compound 3.

d. Synthesis of C-{4-[6-(2-ethoxy-phenyl)-pyrimidin-4-ylamino]-phenyl}-N-methyl-methanesulfonamide (Compound 7)

The same procedure as for Reference compound 3.
Yield: 0.099 g (59%).
Melting point: 218-219° C.
$^{1}$H-NMR (400 MHz, DMSO-$d_6$); δ (ppm) 1.37 (3H, t), 2.58 (3H, d), 4.12 (2H, quart), 4.26 (2H, s), 6.78 (1H, br.

quart), 7.04 (1H, t), 7.13 (1H, d), 7.32 (2H, d), 7.40 (1H, t), 7.46 (1H, s), 7.65 (2H, d), 7.91 (1H, d), 8.67 (1H, s), 9.59 (1H, br. s).
CI MS m/z 399 (MH+)

Example 8

Synthesis of {4-[6-(2-benzyloxy-phenyl)-pyrimidin-4-ylamino]-phenyl}-methanesulfonamide (Compound 8)

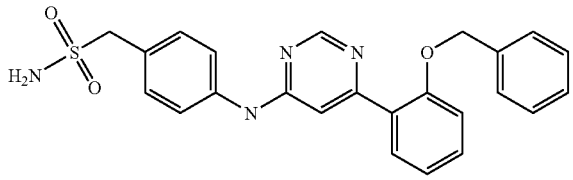 [SMILES: NS(=O)(=O)Cc1ccc(Nc2cc(-c3ccccc3OCc3ccccc3)ncn2)cc1]

a. Synthesis of (4-nitrophenyl)methanesulfonyl amide

The same procedure as for compound 6.

b. Synthesis of (4-aminophenyl)methanesulfonyl amide

The same procedure as for Reference compound 3.

c. Synthesis of 4-chloro-6-(2-benzyloxyphenyl)-pyrimidine

The same procedure as for Reference compound 3.

d. Synthesis of {4-[6-(2-benzyloxy-phenyl)-pyrimidin-4-ylamino]-phenyl}-methanesulfonamide (Compound 8)

The same procedure as for compound 6.
Yield: 0.180 g (81%).
Melting point: 213.7-215.9° C.
$^1$H-NMR (400 MHz, DMSO-$d_6$); δ (ppm) 4.19 (2H, s), 5.23 (2H, s), 6.70 (2H, br. s), 7.05 (1H, t), 7.18 (1H, d), 7.23-7.45 (9H, m), 7.62 (2H, d), 7.82 (1H, d), 8.68 (1H, s), 9.57 (1H, br. s).
CI MS m/z 447 (MH+)

Example 9

Synthesis of {4-[6-(2,3-dimethoxy-phenyl)-pyrimidin-4-ylamino]-phenyl}-methanesulfonamide (Compound 9)

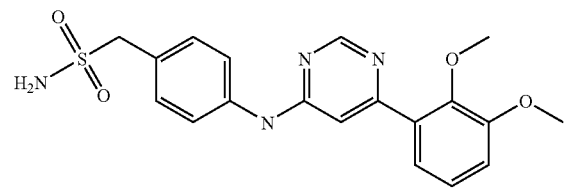 [SMILES: COc1cccc(-c2cc(Nc3ccc(CS(N)(=O)=O)cc3)ncn2)c1OC]

a. Synthesis of (4-nitrophenyl)methanesulfonyl amide

The same procedure as for compound 6.

b. Synthesis of (4-aminophenyl)methanesulfonyl amide

The same procedure as for Reference compound 3.

c. Synthesis of 4-chloro-6-(2,3-dimethoxy-phenyl)-pyrimidine

The same procedure as for Reference compound 3.

d. Synthesis of {4-[6-(2,3-dimethoxy-phenyl)-pyrimidin-4-ylamino]-phenyl}-methanesulfonamide (Compound 9)

The same procedure as for compound 6.
Yield: 0.170 g (85%).
Melting point: 247.8-250.5° C.
$^1$H-NMR (400 MHz, DMSO-$d_6$); δ (ppm) 3.71 (3H, s), 3.83 (3H, s), 4.21 (2H, s), 6.70 (2H, br. s), 7.12 (2H, br. s), 7.32 (3H, br. s), 7.39 (1H, br. s), 7.66 (2H, d), 8.68 (1H, s), 9.61 (1H, br. s).
CI MS m/z 401 (MH+)

Example 10

Synthesis of N,N-diethyl-C-{4-[6-(2-methoxy-phenyl)-pyrimidin-4-ylamino]-phenyl}-methanesulfonamide (Compound 10)

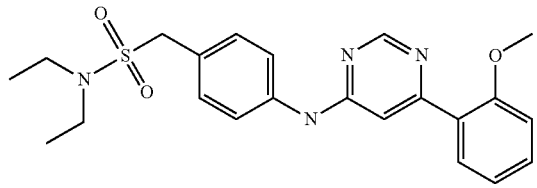 [SMILES: CCN(CC)S(=O)(=O)Cc1ccc(Nc2cc(-c3ccccc3OC)ncn2)cc1]

a. Synthesis of C-(4-nitro-phenyl)-N,N-diethyl-methanesulfonamide

The same procedure as for Reference compound 3.

b. Synthesis of C-(4-amino-phenyl)-N,N-diethyl-methanesulfonamide

The same procedure as for Reference compound 3.

c. Synthesis of 4-chloro-6-(2-methoxyphenyl)-pyrimidine

The same procedure as for Reference compound 3.

d. Synthesis of N,N-diethyl-C-{4-[6-(2-methoxy-phenyl)-pyrimidin-4-ylamino]-phenyl}-methanesulfonamide (Compound 10)

The same procedure as for Reference compound 3.
Yield: 0.070 g (33%).
Melting point: 233.9-235.8° C.

$^1$H-NMR (400 MHz, DMSO-d$_6$); δ (ppm) 1.03 (6H, t), 3.09 (4H, quart), (8H, m), 3.88 (3H, s), 4.30 (2H, s), 7.07 (1H, t), 7.17 (1H, d), 7.33 (2H, d), 7.40-7.47 (2H, m), 7.71 (2H, d), 7.94 (1H, d), 8.68 (1H, s), 9.61 (1H, br. s).
CI MS m/z 427 (MH+)

Example 11

Synthesis of C-{4-[6-(2-benzyloxy-phenyl)-pyrimidin-4-ylamino]-phenyl}-N-methyl-methanesulfonamide (Compound 11)

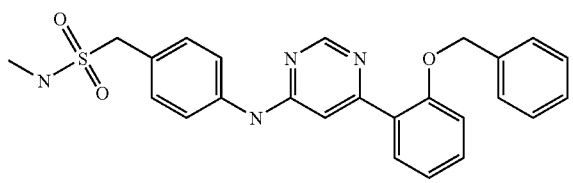 [SMILES: CNS(=O)(=O)Cc1ccc(Nc2cc(-c3ccccc3OCc3ccccc3)ncn2)cc1]

a. Synthesis of (4-nitrophenyl)-N-methylmethanesulfonamide

The same procedure as for Reference compound 4.

b. Synthesis of (4-aminophenyl)-N-methylmethanesulfonamide

The same procedure as for Reference compound 3.

c. Synthesis of 4-chloro-6-(2-benzyloxyphenyl)-pyrimidine

The same procedure as for Reference compound 3.

d. Synthesis of C-{4-[6-(2-benzyloxy-phenyl)-pyrimidin-4-ylamino]-phenyl}-N-methyl-methanesulfonamide (Compound 11)

The same procedure as for Reference compound 3.
Yield: 0.164 g (70%).
Melting point: amorphous behavior, softening above 85° C.
$^1$H-NMR (400 MHz, DMSO-d$_6$); δ (ppm) 2.58 (3H, d), 4.26 (2H, s), 5.22 (2H, s), 6.78 (1H, br. quart), 7.06 (1H, t), 7.18 (1H, d), 7.23-7.45 (9H, m), 7.62 (2H, d), 7.82 (1H, d), 8.69 (1H, s), 9.56 (1H, br. s).
CI MS m/z 461 (MH+)

TABLE 3

Reference Examples 3-4 and Examples 6-11: Yields of the intermediates

| (nitrophenyl) methanesulfonamide | Yield % | (aminophenyl) methanesulfonamide | Yield % | 4-chloro-6-aryl-pyrimidine | Yield % |
|---|---|---|---|---|---|
| | 72 | | 50 | | 70 |
| | 90 | | 95 | | 73 |
| | 65 | | 75 | | 42 |
| | 91 | | 95 | | 60 |

TABLE 3-continued

Reference Examples 3-4 and Examples 6-11: Yields of the intermediates

| (nitrophenyl)methanesulfonamide | Yield % | (aminophenyl)methanesulfonamide | Yield % | 4-chloro-6-aryl-pyrimidine | Yield % |
|---|---|---|---|---|---|
| [structure] | 39 | [structure] | 54 | | |

Example 12

I. Behavioral Animal Models for the Analysis of Inflammatory and Neuropathic Pain Several animal models for the analysis of inflammatory and neuropathic pain are known. Said models share the common feature that after e.g., induction of a nerve lesion (e.g., spared nerve injury, SNI) or after exposing experimental animals to a noxious stimulus (e.g., injection of formalin or carrageenan), the signs of pain as induced by said interventions are measured by quantifiable behavioral components such as, e.g., paw withdrawal threshold to mechanical stimulation with von Frey hairs (or to thermal stimulation using a laser source or licking behaviour). These reactions are interpreted as being equivalent to mechanical and thermal allodynia (hypersensitivity to mechanical stimuli) or hyperalgesia in humans.

The spared nerve injury model (SNI model, as developed by Decosterd and Woolf (2000), see FIG. 1) is characterized by the induction of clinically relevant nerve lesions and after surgical intervention, subsequent behavioral experiments (e.g., von Frey Assay). Said model constitutes a common nerve injury model which consists of ligation and section of two branches of the sciatic nerve (namely tibial and common peroneal nerves) leaving the sural nerve intact. The SNI model results in early (less than 24 hours), prolonged and substantial changes in mechanical and cold sensitivity that closely mimic the features of clinical neuropathic pain. Animals with these types of nerve injury have been shown to develop abnormal pain sensations and hypersensitivity to mechanical stimuli (allodynia) similar to those reported by neuropathic pain patients. Alternatively, the formalin assay in mice is a valid and reliable behavioral model of nociception in inflammatory and neuropathic pain. It is sensitive to various classes of analgesic drugs (Hunskaar S, Hole K, Pain. 1987 July; 30(1):103-14.) The noxious stimulus consists of an injection of 10 µl diluted formalin (2% in saline) under the skin of the dorsal surface of the left hindpaw (subcutaneous or interplantar into the left hindpaw). The response is licking and flinching of the injected paw.

For the carrageenan assay a subcutaneous injection of 25 µl of 1% carrageenan (in saline) into a single hind paw (ipsilateral paw) of mice is applied. Subsequent inflammation results in long lasting swelling and hypersensitivity (against mechanical and thermal stimuli) of the paw. The carrageenan assay is a standard laboratory assay used to predict anti-inflammatory activity of test compounds. Paw edema measurements and Hargreaves Assay (withdrawal of paws due to thermal stimulation via a light source) are used for read out.

Regarding the present invention, the effect of administration of CDK5-inhibiting compounds according to Formula I on the development of inflammatory and neuropathic pain could be assayed in a SNI model, in a carrageenan and in a formalin assay.

Example 13

A. Spared Nerve Injury (SNI)

Model of Chronic Neuropathic Pain

As outlined above, the spared nerve injury (SNI) model (see FIG. 1) involves a lesion of two of the three terminal branches of the sciatic nerve (tibial and common peroneal nerves) of experimental animals, leaving the sural nerve intact. SNI results in mechanical and thermal allodynia in the non-injured sural nerve skin territory (Decosterd and Woolf, Pain 2000; 87:149-158. (2) Tsujino et al., Mol. Cel. Neurosci. 2000; 15:170-182).

1. Induction of Spared Nerve Injury (Nerve Lesion) in Wildtype Mice

Wildtype mice (strain C3HeB/FeJ) (age, sex and weight matched) were anesthetized with Hypnorm (0.315 mg/ml fentanyl citrate+10 mg/ml fluanisone; Janssen)/Hypnovel (5 mg/ml midazolam; Roche Applied Sciences)/water at a ratio of 1:1:2 at 4 µl/g prior to surgical preparation.

Subsequently, an incision was made under aseptic precautions in the ipsi-lateral right hind leg of all mice just above the level of the knee, exposing the three terminal branches of the sciatic nerve: the common peroneal, tibial, and sural nerves. The common peroneal and tibial nerves were ligated tightly with 7/0 silk and sectioned distal to the ligation removing ≈2 mm of distal nerve stump. The sural branch remained untouched during the procedure (denoted herein "SNI ipsi"). The overlying muscle and skin was sutured, and the animals were allowed to recover and to permit wound healing. In the same mice the sciatic nerve branches of the contra-lateral left hind leg were exposed but not lesioned (denoted herein "SNI contra-lateral"). Mice that underwent spared nerve injury are hereinafter denoted "SNI mice".

2. Administration of CDK-Inhibiting Compounds to SNI Mice

After recovery from surgery and wound healing, SNI mice received per oral (p.o.) injections of CDK-inhibiting compounds.

30 mg/kg of a CDK inhibitor, dissolved in 400 µl of 2% Hydroxprolylcellulose; 0.25% Lactic Acid (85% solution) was administered via per oral application 30 min prior to von Frey measurements (mechanical allodynia). As a negative control, the same amount (400 µl) of 2% Hydroxprolylcellulose; 0.25% Lactic Acid (85% solution) vehicle was administered by a single per oral application 30 min prior to von Frey measurements.

Injection of inhibitor or vehicle, and subsequent measurements of paw withdrawal threshold to mechanical stimulation in von Frey assays were performed at day 107 post SNI. Reflex nociceptive responses to mechanical stimulation were measured in a von Frey assay 30 min after each injection.

The effect of administration of CDK inhibitors to SNI mice on the development of mechanical allodynia was analyzed in a von Frey assay, as described below.

3. Behavioral Testing of SNI Mice after Administration of CDK-Inhibiting Compounds (Von Frey Assay)

Mice that underwent SNI and subsequent administration of the compounds of the present invention were tested for signs of mechanical allodynia post nerve injury and post administration in a von Frey assay (Decosterd and Woolf, Pain 2000; 87:149-158). This assay determines the mechanical threshold upon which a stimulus, which normally is not painful, is recognized by an animal as uncomfortable or painful. SNI ipsi and SNI contra baselines, respectively, were established.

Mechanical thresholds of SNI mice were quantified using the up-down method based on Chaplan et al. (1994) and Malmberg and Basbaum (1998).

Mice were placed in plexiglass cylinders of about 9.5 cm in diameter, 14 cm high with four vent holes toward the top and a plexiglass lid. The cylinders were placed on an elevated mesh surface (7×7 mm squares). Prior to the day of testing, the mice were acclimated to the testing cylinders for 1-2 hours. On the day of testing the mice were acclimated to the cylinders for about an hour, wherein the acclimation time depends on factors such as the strain of the mouse and the number of times they have been tested previously. In general, testing may begin once the mice are calm and stop exploring the new environment.

For testing mice, filaments 2.44, 2.83, 3.22, 3.61, 3.84, 4.08, and 4.31 (force range=0.04 to 2.0 g) were used. The 3.61 mN filament was applied first. Said filament was gently applied to the plantar surface of one paw, allowed to bend, and held in position for 2-4 seconds. Whenever a positive response to the stimulus (flexion reaction) occurred the next weaker von Frey hair was applied; whenever a negative response (no reaction) occurred the next stronger force was applied. The test was continued until the response to 4 more stimuli after the first change in response had been obtained. The highest force tested was 4.31. The cut-off threshold was 2 g.

The series of scores (i.e, "flexion reaction" and "no reaction") and the force of the last filament applied were used to determine the mechanical threshold as described in Chaplan et al., Journal of Neuroscience Methods. 53(1):55-63, 1994 July The threshold determined is that to which the animal would be expected to respond to 50% of the time. Mice were sacrificed after von Frey measurements were accomplished.

4. Effects of Administration of CDK-Inhibiting Compounds on the Development of Neuropathic Pain CDK-inhibiting compounds were administered to SNI mice as described above. Von Frey measurements were performed at ipsi-lateral and contra-lateral paws of the animals at day 107 after surgery as described above. Without pharmacological treatment SNI mice show a stable allodynia after SNI surgery. Animals treated with compound display a significant increase of threshold values indicating reduced sensitivity to mechanical stimuli (reduced allodynia). The observation of reduced allodynia signify that a CDK-inhibiting compound is effective as a hypoalgesic drug in models of chronic neuropathic pain.

Example 14

Formalin Assay

Model of Inflammatory Processes/Inflammatory and Chronic Neuropathic Pain

The formalin assay in mice is a valid and reliable behavioral model of nociception and is sensitive to various classes of analgesic drugs (Hunskaar S, Hole K, Pain. 1987 July; 30(1):103-14.) The noxious stimulus is an injection of 10 µl diluted formalin (2% in saline) subcutaneous or intraplantar into the left hind paw. The response is licking and flinching of the injected paw. The response shows two phases, which reflect different parts of the inflammatory process (Abbott et al 1995), an early/acute phase 0-5 min post-injection, and a late/chronic phase 5-30 min post-injection. The following protocol describes one possible way to conduct the experiment:

1. Injection of Formalin and Administration of CDK-Inhibiting Compound

Age, sex and weight matched wildtype mice (C3HeB/FeJ) are used in this assay. Prior to formalin injection the animals are randomly subdivided into experimental groups of 10 animals each. Thirty minutes prior to formalin injection, a suitable dose of a CDK inhibitor dissolved in (400 µl) of 2% Hydroxprolylcellulose; 0.25% Lactic Acid (85% solution)) can be administered by i.p. injection. Similarly, Iκ Kinase (IKK) inhibitor (30 mg/kg) in (400 µl) of 2% Hydroxprolylcellulose; 0.25% Lactic Acid (85% solution) (positive control), or vehicle alone ((400 µl) of 2% Hydroxprolylcellulose; 0.25% Lactic Acid (85% solution)) (negative control) can be administered by i.p. injection 30 min before formalin injection.

For formalin injection the mouse is held with a paper towel, in order to avoid disturbance of the injection by movements. The injected hind paw is held between thumb and forefinger and 10 µl of Formalin (2%) is injected subcutaneously (s.c.) between the two front tori into the plantar hind paw using a Hamilton syringe. The behavior of the formalin- and inhibitor-treated mice is analyzed as described below.

2. Behavioral Analysis of Mice after Injection of Formalin and Administration of CDK-Inhibiting Compound The behaviour of the formalin-treated mice, i.e. licking and flinching, is monitored by an automated tracking system (Ethovision 3.0 Color Pro, Noldus, Wageningen, Netherlands) over a defined period of time: measurement is initiated 5 min after formalin injection and terminated 30 min after formalin injection. This time frame covers phase II of formalin-induced nociception (pain), which is hyperalgesia.

Two different fluorescent dyes are used for topically marking the injected hind paw (yellow dye) (Lumogenyellow; BASF Pigment, Cologne, Germany) and the contralateral paw (blue dye) (Lumogenviolet; Kremer Pigmente, Aichstetten, Germany) respectively. To determine licking behaviour, mice are monitored with a CCD camera. After monitoring and recording, the video is analyzed using the EthoVision software (Ethovision 3.0 Color Pro, Noldus, Wageningen, Netherlands) or by manual analysis. Fluorescent dot sizes and fluorescence intensities were measured and reduction of fluorescent dot size through licking and biting was calculated. The overall licking time intensity was automatically calculated by comparison of dot size reduction of treated versus untreated paws.

As another variant of assay read out the licking behaviour of the individual animals was tracked manually based on video files. Licking times were recorded over 30 minutes after formalin injection and subdivided for three different licking zones (dorsum, plantar, toes). Overall licking times can be calculated for each animal as well as each experimental group and be used as a parameter for determination of compound efficacy.

As a result it was found that mice receiving vehicle treatment prior to formalin injection (negative control) displayed a prolonged licking time and a significant reduction of fluorescent dot size at the formalin-treated paw.

Observation of a reduction in licking time and in consequence no significant reduction of fluorescent dot size of the formalin-treated paw regarding test compound/formalin-treated mice is an indication of relief of pain and inflammation.

Example 15

Carrageenan Assay in Mice

Model of Inflammation and Inflammatory Pain

The model of carrageenan induced paw edema is a standard laboratory assay used to predict anti-inflammatory activity and reduction of inflammation-induced pain perception of respective compounds. The following protocol describes one possible way to conduct the experiment.

The basic measurement constitutes in the measurement of edema and mechanical as well as thermal hypersensitivity in response to irritants, such as carrageenan. Inflammation and resulting inflammatory pain is induced by subcutaneous injection of 25 µl of 1% carrageenan (in saline) into mice hind paw (ipsi-lateral paw). Each group of 10 mice receives administration of a compound according to Formula I, 30 mg/kg body weight, vehicle ((400 µl) of 2% Hydroxprolyl-cellulose; 0.25% Lactic Acid (85% solution)) and saline (physiol. NaCl) by i.p. injection 30 min prior to carrageenan injection. Contra-lateral paws do not receive carrageenan injection.

1.1 Effects of Administration of a CDK5-Inhibiting Compound on Carrageenan-Treated Mice Paw edema induced by carrageenan injection are detected by increased paw size measured from dorsal to plantar at the metatarsus region of the injected (ipsi-lateral) paws. Sizes of ipsi- and contra-lateral paws serve as surrogate markers for inflammation and are measured at several time points after carrageenan injection: before injection (−1), 2 h (2), 3 h (3) 4 h (4), 5 h (5), 6 h (6), 24 h (24) after injection.

The paw size of all mice may increase, e.g., by 2 to 3 mm (+10%) within the first hour after carrageenan injection, independent of the type of treatment substance injected 30 minutes prior to carrageenan. During the time course, mice which received treatment with a CDK-inhibiting compound prior to carrageenan injection may display a reduction of the edema until 24 h after carrageenan injection: the increase in paw size could drop e.g. from 10% down to 8%. In contrast, the paw size of the control mice could increase by 30% in average at this time point. After 24 h post carrageenan injection, the size of all paws treated with carrageenan may increase to reach its maximum at 96 h after injection.

As a read-out of the carrageenan assay, a Hargreaves Assay may be performed, wherein said assay allows the measuring of thermal sensitivity to radiant heat. The Hargreaves assay (Hargreaves et al., 1988) measures nociceptive sensitivity in a freely moving animal by focusing a radiant heat source on the plantar surface of an animal's hindpaw as it stands in a plexiglass chamber. Specifically, the lower side of a paw is exposed to a luminous source, generating a temperature of, e.g. 55° C. Thermal sensitivity is measured as latency between start of exposure and lifting/pulling the exposed paw.

Mice treated with a CDK5 inhibitor as disclosed herein and carrageenan, or with Naproxen and carrageenan, or with solvent and carrageenan, respectively, are subjected to a Hargreaves assay. Mice treated with a CDK5 inhibitor and carrageenan could display a longer latency, compared to negative control mice. This observation would be indicative for a hypoalgesic effect of the CDK5 inhibitors as disclosed herein.

Example 16

Carrageenan Assay in Rats

Model of Inflammation and Inflammatory Pain

The following depicts one possible way of performing the carrageenan assay in rats.

Said assay detects analgesic/anti-inflammatory activity in rats with inflammatory pain, following the protocol as described by Winter et al (Proc. Soc. Exp. Biol. Med., 111, 544-547, 1962).

Rats (200-250 g) are injected with a suspension of carrageenan into the lower surface of the right hindpaw (0.75 mg per paw in 0.05 ml physiological saline). Two hours later rats are submitted consecutively to tactile and thermal stimulation of both hindpaws.

For tactile stimulation, the animal is placed under an inverted acrylic plastic box (18×11.5×13 cm) on a grid floor. The tip of an electronic Von Frey probe (Bioseb, Model 1610) is then applied with increasing force first to the non-inflamed and then the inflamed hindpaw and the force required to induce paw-withdrawal is automatically recorded. This procedure is carried out 3 times and the mean force per paw is calculated.

For thermal stimulation, the apparatus (Ugo Basile, Reference: 7371) consists of individual acrylic plastic boxes (17× 11×13 cm) placed upon an elevated glass floor. A rat is placed in the box and left free to habituate for 10 minutes. A mobile infrared radiant source ($96 \pm 10$ mW/cm$^2$) is then focused first under the non-inflamed and then the inflamed hindpaw and the paw-withdrawal latency is automatically recorded. In order to prevent tissue damage the heat source is automatically turned off after 45 seconds.

After the behavioral measures, the paw edema is evaluated by measuring the volume of each hindpaw using a digital plethysmometer (Letica, Model 7500), which indicates water displacement (in ml) induced by paw immersion.

10 rats are studied per group. The test is performed blind.

The test substance, such as a CDK5 inhibitor according to Formula I as presented herein, will be evaluated at 2 doses (10 and 30 mg/kg), administered p.o. 60 minutes before the test, and compared with a vehicle control group.

Morphine (128 mg/kg p.o.) and acetylsalicylic acid (512 mg/kg p.o.), administered under the same experimental conditions, will be used as reference substances.

The experiment will therefore include 6 groups. Data will be analyzed by comparing treated groups with vehicle control using unpaired Student's t tests.

Rats treated with a CDK5 inhibitor as disclosed herein and carrageenan, or with Naproxen and carrageenan, or with solvent and carrageenan, respectively, are subjected to a Hargreaves assay. Rats treated with a CDK inhibitor and carrageenan should display a longer latency, compared to negative control rats. This observation would be indicative for a hypoalgesic effect of the CDK5 inhibitors as disclosed herein.

Example 17

A. In Vitro Kinase Inhibition Assays

IC50 profiles of compounds #1-28 were determined for cyclin-dependent kinases CDK2/CycA, CDK4/CycD1, CDK5/p35NCK, CDK6/CycD1 and CDK9/CycT in enzymatic kinase inhibition assays in vitro. IC50 values as obtained in these assays were used for evaluating the specific selectivity and potency of the compounds with respect to CDK9 inhibition.

Results obtained in these assays were used to select compounds displaying specificity for CDK5. Specifically, it was intended to distinguish the CDK5-specific compounds from other compounds having significant inhibitory potency also with regard to other CDKs, i.e. on some or all of CDKs 2, 4, 6, and 9. This separation is essential in order to avoid adverse (cytostatic/cytotoxic) effects, which may occur upon inhibition of cell cycle relevant CDKs 2, 4, 6, and 9.

Furthermore, these data were used to establish structure activity relationships (SAR) supporting the design of new and even improved structures/compounds with respect to potency and selectivity.

1. Test Compounds

Compounds were used as $1\times10^{-02}$ M stock solutions in 100% DMSO, 100 µl each in column 2 of three 96-well V-shaped microtiterplates (in the following, said plates are referred to as "master plates").

Subsequently, the $1\times10^{-02}$ M stock solutions in column 2 of the master plates were subjected to a serial, semi-logarithmic dilution using 100% DMSO as a solvent, resulting in 10 different concentrations, the dilution endpoint being $3\times10^{-07}$ M/100% DMSO in column 12. Column 1 and 7 were filled with 100% DMSO as controls. Subsequently, 2×5 µl of each well of the serial diluted copy plates were aliquoted in 2 identical sets of "compound dilution plates", using a 96-channel pipettor.

On the day of the kinase inhibition assay, 45 µl $H_2O$ were added to each well of a set of compound dilution plates. To minimize precipitation, the $H_2O$ was added to the plates only a few minutes before the transfer of the compound solutions into the assay plates. The plates were shaken thoroughly, resulting in "compound dilution plates/10% DMSO" with a concentration of $1\times10^{-03}$ M/10% DMSO to $3\times10^{-08}$ M/10% DMSO in semilog steps. These plates were used for the transfer of 5 µl compound solution into the "assay plates". The compound dilution plates were discarded at the end of the working day. For the assays (see below), 5 µl solution from each well of the compound dilution plates were transferred into the assay plates. The final volume of the assay was 50 µl. All compounds were tested at 10 final assay concentrations in the range from $1\times10^{-04}$ M to $3\times10^{-09}$ M. The final DMSO concentration in the reaction mixtures was 1% in all cases.

2. Recombinant Protein Kinases

For the determination of inhibitory profiles, the following 5 protein kinases were used: CDK2/CycA, CDK4/CycD1, CDK5/p35NCK, CDK6/CycD1 and CDK9/CycT. Said protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity of each kinase was determined by SDS-PAGE/silver staining and the identity of each kinase was verified by western blot analysis with kinase specific antibodies or by mass spectroscopy.

3. Protein Kinase Assay

All kinase assays were performed in 96-well FlashPlates™ from Perkin Elmer/NEN (Boston, Mass., USA) in a 50 µl reaction volume. The reaction mixture was pipetted in four steps in the following order:

20 µl of assay buffer (standard buffer)

5 µl of ATP solution (in $H_2O$)

5 µl of test compound (in 10% DMSO)

10 µl of substrate/10 µl of enzyme solution (premixed)

The assay for all enzymes contained 60 mM HEPES-NaOH, pH 7.5, 3 mM $MgCl_2$, 3 mM $MnCl_2$, 3 µM Na-Orthovanadate, 1.2 mM DTT, 50 µg/ml PEG20000, 1 µM [$\gamma$-$^{33}$P]-ATP (approx. 5×1005 cpm per well).

The following amounts of enzyme and substrate were used per well:

| # | Kinase | Kinase Lot # | Kinase ng/50 µl | Substrate | Substrate ng/50 µl |
|---|---|---|---|---|---|
| 1 | CDK2/CycA | SP005 | 100 | Histone H1 | 250 |
| 2 | CDK4/CycD1 | SP005 | 50 | Rb-CTF (Lot 009) | 500 |
| 3. | CDK5/p35NCK | SP001 | 50 | Rb-CTF (Lot 009) | 1000 |
| 3 | CDK6/CycD1 | SP003 | 400 | Rb-CTF (Lot 009) | 500 |
| 4 | CDK9/CycT | 003 | 100 | Rb-CTF (Lot 009) | 1000 |

Reaction mixtures were incubated at 30° C. for 80 minutes. The reaction was stopped with 50 µl of 2% (v/v) $H_3PO_4$, plates were aspirated and washed two times with 200 µl $H_2O$ or 200 µl 0.9% (w/v) NaCl. Incorporation of $^{33}$P was determined with a microplate scintillation counter (Microbeta, Wallac).

All assays were performed with a BeckmanCoulter/Sagian robotic system.

4. Evaluation of Raw Data

The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was referred to as 100% activity. As part of the data evaluation, the low control value from a particular plate was subtracted from the high control value as well as from all 80 "compound values" of the corresponding plate. The residual activity (in %) for each well of a particular plate was calculated by using the following formula:

$$\text{Res. Activity}(\%)=100\times[(\text{cpm of compound–low control})/(\text{high control–low control})]$$

The residual activities for each concentration and the compound IC50 values were calculated using Quattro Workflow V2.0.1.3 (Quattro Research GmbH, Munich, Germany; www.quattro-research.com). The model used was "Sigmoidal response (variable slope)" with parameters "top" fixed at 100% and "bottom" at 0%.

It turns out that IC50 values for compounds #1-28 all can be found within the range of 1 nM-10 µM.

Example 18

In Vitro SH-SY5Y Assay

Using Tau Phosphorylation to Characterize CDK5 Inhibitors

Introduction

Abnormal tau phosphorylation and deregulated CDK5/p35 activity are closely linked to each other and represent hallmarks of neurodegenerative diseases such as Alzheimer's disease, Parkinson's disease or Amyotrophic lateral sclerosis.

The human neuroblastoma cell line SH-SY5Y can be utilized as an in vitro model to investigate CDK5 function and the efficacy of CDK5 specific inhibitors. SH-SY5Y cells express tau protein which harbors various phosphorylation sites known to be phosphorylated by several kinases including CDK5. SH-SY5Y cells can be differentiated into neuron-like cells by exposure to 10 µM all trans-retinoic acid for 3 days and subsequent exposure to 50 ng/ml human recombinant brain-derived neurotrophic factor for 3-5 days, thereby upregulating neuronal markers, including tau protein. In addition CDK5 and p35 protein levels were increased during differentiation. RA-BDNF-differentiated cells can therefore serve as a suitable model for studying tau phosphorylation and to screen potential CDK5 inhibitors (Jämsä et al., 2004. BBRC 319; 993-1000).

1. Growth and Differentiation of SH-SY5Y Cells

SH-SY5Y neuroblastoma cells (ATCC, CRL-2266) are grown in DMEM supplemented with 15% FCS and 1% Pen/Strep at 37° C. and 5% $CO_2$. For differentiation, cells are seeded at a density of $2 \times 10^5$ cells/6-well in normal growth medium and incubated overnight to attach. Differentiation is induced by replacing normal growth medium with antibiotic-free growth medium supplemented with 10 µM all trans-retinoic acid (RA, dissolved in DMSO; Sigma-Aldrich, R2625) and further incubation for 3 days. Subsequently the medium is changed to serum- and antibiotic-free medium supplemented with 50 ng/ml human recombinant brain-derived neurotrophic factor (BDNF, dissolved in sterile $ddH_2O$; Sigma-Aldrich, B3795) and cells are incubated for another 3-5 days to complete differentiation.

Alternative Assays and Readouts to Characterize CDK5 Inhibitors

Alternatively, instead of SH-SY5Y cells human IMR-32 neuronal cells differentiated with 10 µM BrdU for 3 days or rat PC12 neuroblastoma cells differentiated with 50 ng/ml human recombinant nerve growth factor (NGF) for 3 days can be used to study tau phosphorylation at various phosphorylation sites.

IMR-32 neuroblastoma cells (DSMZ, ACC 165) are grown in RPMI supplemented with 20% FCS, 1% non-essential amino acids and 1% Pen/Strep at 37° C. and 5% $CO_2$. For differentiation cells are seeded at a density of $1 \times 10^6$ cells/6-well in normal growth medium and incubated overnight to attach. Differentiation is induced by replacing normal growth medium with antibiotic-free growth medium supplemented with 10 µM (+)-5-Bromo-2'-deoxyuridine (BrdU, dissolved in sterile PBS; Sigma Aldrich, 858811) and further incubation for 3 days.

PC12 neuroblastoma cells (DSMZ, ACC 159) are grown in RPMI1640 supplemented with 10% horse serum, 5% FCS and 1% Pen/Strep in culture flasks coated with rat tail collagen (Roche, 11 179 179 001). To induce differentiation to neuron-like cells, medium is changed to serum- and antibiotic-free medium supplemented with 50 ng/ml human recombinant nerve growth factor (NGF) and further incubation for 3 days.

(C2C12 myoblasts are grown in DMEM supplemented with 10% FCS and 1% Pen/Strep. For differentiation cells are seeded at a density of $1.25 \times 10^5$ cells/12-well in normal growth medium and incubated to confluency. Differentiation is induced by replacing normal growth medium with DMEM supplemented with 2% horse serum and 1% Pen/Strep for 2-5 days.)

2. Treatment of Differentiated SH-SY5Y Cells with CDK-Inhibiting Compounds

After differentiation is completed, the medium is replaced with serum-free growth medium with CDK-inhibiting compounds as well as reference compounds such as positive and negative controls, each dissolved in DMSO, are added at concentrations ranging from 0.1 to 100 µM (final concentration of DMSO in the well should be 0.1%). Cells are incubated for 90-120 min with compounds. Cells are harvested by scraping, washed twice with PBS and lysed in lysis buffer (BioSource, FNN0011). Lysed cells are stored at −20° C. or used immediately for Western Blot or ELISA assay to determine total tau and pS396 or pT231 tau.

3. Determination of Total and ptau Contents in SH-SY5Y Cell Lysates after Administration of CDK-Inhibiting Compounds Concentrations of total tau, pS396 tau and pT231 tau within the cell culture lysates are measured by using commercial ELISA Kits (BioSource: human total tau: KHB0042; human pS396 tau: KHB7031; human pT231 tau: KHB7051) according to the manufacturers instructions or by using Western Blots probing with total and phospho-specific antibodies (antibodies: total tau: Santa Cruz, sc-21796; pS396 tau: Santa Cruz, sc-12414; pT231 tau, AT180: Pierce Endogen, MN1040; pS202 tau: AT8: Pierce Endogen, MN1020).

4. Effects of CDK-Inhibiting Compound #8 on Phosphorylation of Tau protein at Serin396 in Differentiated SH-SY5Y Cells CDK5-inhibitory compounds were dissolved in DMSO and administered to RA- and BDNF-differentiated SH-SY5Y cells in duplicates or triplicates. After 90-120 min of incubation with test or reference compounds (e.g. LiCl, a GSK3β inhibitor or roscovitine, a CDK inhibitor), cells were harvested for Western Blot or ELISA analysis as described above.

Cells treated with compound #8 displayed a significant inhibitory effect of compound #8 on Tau phosphorylation at Serin396. Compared to reference compounds LiCl and roscovitine, this compound exhibited a similar or better inhibition of Tau phosphorylation at S396.

4. Alternative Assays and Readouts

Alternative assays: human SH-SY5Y cells (differentiated with RA and BDNF) human IMR-32 neuronal cells (differentiated with BrdU) and mouse C2C12 myoblasts (differentiated to myotubes with DMEM supplemented with 2% horse serum and 1% Pen/Strep for 2-5 days) express the transcription factor MEF2D which is a known substrate of CDK5. CDK5/p35 phosphorylates and thereby inhibit MEF2D transcriptional activity. Inhibition of CDK5 will therefore decrease MEF2D transcriptional activity. Cellular assays reading out MEF2D activity (e.g. using a reporter gene assay, an activity ELISA (Panomics, TransBinding MEF2 Assay kit, EK1081) or in Western Blots using pMEF2D and total MEF2D antibodies) will be useful tools to measure CDK5 activity. Similar readouts using transcriptional activity of Stat3, another known substrate of CDK5/p35 can be used (Fu et al., 2004. PNAS, vol 101(17); 6728-6733).

REFERENCES

Barboric M. et al., NfkB Binds P-TEFb to Stimulate Transcriptional Elongation by RNA Polymerase II. *Molecular Cell,* 2001, Vol. 8, 327-337

Besson J. M., The neurobiology of pain. *Lancet,* 1999, 353 (9164), 1610-1615

Brower, New paths to pain relief. *Nat Biotechnol,* 2000, 18(4), 387-391

Chao S. H. and Price D. H., Flavopiridol inactivates P-TEFb and blocks most RNA polymerase II transcription in vivo. *J Biol Chem,* 2001, 276(34), 31793-9

Chaplan S R, Bach F W, Pogrel J W, Chung J M, and Yaksh, T L. (1994) Quantitative assessment of tactile allodynia in the rat paw. *J Neurosci Methods* 53: 55-63.

Dai Y. and Grant S., Cyclin-dependent kinase inhibitors. *Curr Opin Pharmacol,* 2003, 3(4), 362-370

Falco G. D. et al., CDK9, a member of the cdc2-like family of kinases, binds to gp130, the receptor of the IL-6 family of cytokines. *Oncogene,* 2002, 21(49), 7464-7470

Feldmann and Maini, NatMed, 2003, 9 (10); 356-61

Firestein, 2003, Nature 423, 356-361

Han et al.; 2003, Autoimmunity, 28, 197-208

Hargreaves, K: *Pain* 32(1) (1988 January) 77-88

Huwe et al., Small molecules as inhibitors of cyclin-dependent kinases. *Angew Chem Int Ed Engl,* 2003, 42(19), 2122-2138

Kim et al., Phosphorylation of the RNA polymerase II carboxyl-terminal domain by CDK9 is directly responsible for human immunodeficiency virus type 1 Tat-activated transcriptional elongation. *Mol Cell Biol,* 2002, 22(13), 4622-4637.

Koltzenburg M, Neural mechanisms of cutaneous nociceptive pain. *Clin J Pain,* 2000, 16(3 Suppl), 131-138

Laufer S., Gay S. And Brune K., Inflammation and Rheumatic Diseases—The molecular basis of novel therapies, Thieme, 2003

Lee K. M. et al., Spinal NfkB activation induces COX-2 upregulation and contributes to inflammatory pain hypersensitivity. *European Journal of Neuroscience,* 2004, Vol. 19, 3375-3381

Liu H. and Herrmann C., Differential Localization and Expression of the CDK9 42k and 55k Isoforms. *J Cell Physiol,* 2004, 203, 251-260

MacLachlan T. K. et al., Binding of CDK9 to TRAF2. *J Cell Biochem,* 1998, 71(4), 467-478

Malmberg A B and Basbaum A I. (1998) Partial sciatic nerve injury in the mouse as a model of neuropathic pain: behavioral and neuroanatomical correlates. *Pain* 76: 215-2

Meijer L, Leclerc S., Leost M., Properties and potential applications of chemical inhibitors of cyclin-dependent kinases, Pharmacol Ther 1999, 82(2-3):279-284

Sausville, E. A. Trends Molec. Med. 2002, 8, S32-S37

Tian B. et al., Identification of direct genomic targets downstream of the NfkB transcription factor mediating TNF signaling. *JBC,* 2005, as manuscript M500437200

Wang D, et al., Inhibition of human immunodeficiency virus type 1 transcription by chemical cyclin-dependent kinase inhibitors. J. Virol. 2001; 75: 7266-7279

Watkins L. R. et al., Glial proinflammatory cytokines mediate exaggerated pain states: implications for clinical pain. *Adv Exp Med. Biol.,* 2003, 521, 1-21

West et al.; 2001, Journal of Virology 75(18), 8524-8537

Zhou M. et al., Coordination of transcription factor phosphorylation and histone methylation by the P-TEFb Kinase during human immunodeficiency virus type I transcription, J. Virol 2004, 78(24):13522-13533

The invention claimed is:
1. A compound according to the general Formula I:

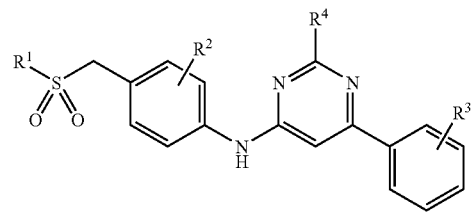

Formula I wherein
$R^1$ is selected from the group consisting of —$NR^5R^6$, —$R^8$, —$C_{1-4}$ alkyl-OH, and —$C_{2-4}$-alkylene-O—$C_{1-4}$ alkyl;
wherein
$R^5$ and $R^6$ independently of each other are selected from the group consisting of hydrogen, $C_{1-4}$ alkyl, $C_{2-4}$ alkenyl, hydroxy-$C_{1-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkylene, $C_{4-7}$ aryl-$C_{0-4}$ alkylene, and $C_{4-7}$ heteroaryl-$C_{0-4}$ alkylene, or
wherein $R^5$ and $R^6$ together with the N-atom to which they are bound also form a 5- to 8-membered heterocycloalkyl or a 5- to 6 membered heteroaryl,
wherein said cycloalkyl, heterocycloalkyl, aryl, heteroaryl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O—, and —$NR^5R^6$;
$R^8$ is $C_{1-4}$ alkyl, $C_{2-4}$ alkenyl, hydroxy-$C_{2-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkyl;
wherein said cycloalkyl, heterocycloalkyl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O, and —$NR^5R^6$;
$R^2$ can be 0 to 2 independent halo substituents;
$R^3$ can be 1 to 3 substituents independently selected from the group consisting of hydrogen, halo, hydroxy, $C_{1-4}$alkyl, $C_{3-7}$cycloalkyl, $C_{1-4}$ alkyl-cycloalkyl, $C_{1-4}$ alkyl-heterocycloalkyl, —O-heterocycloalkyl, $C_{1-4}$ alkoxy, $C_{1-4}$ alkenyloxy, —$OCF_3$, $C_{2-4}$ alkanoyl, $C_{1-4}$-alkylsulfonyl, mono- and di-($C_1$-$C_4$alkyl)sulfonamido, aminocarbonyl, mono- and di-($C_1$-$C_4$alkyl)aminocarbonyl, alkoxy, heteroaryl-$C_{1-4}$ alkoxy, heterocycloalkyl-$C_{1-4}$ alkoxy, heterocycloalkyl-$C_{1-4}$ alkyl, heteroaryl-$C_{1-4}$-alkyl, $C_{1-4}$ alkyloxymethyl, hydroxy-$C_{1-4}$ alkyloxymethyl, cyano, —COOH, and $C_1$-$C_4$ alkoxycarbonyl, wherein the above mentioned substituents can be further substituted by radicals selected from the group consisting of $C_{1-4}$-alkyl, hydroxyl-$C_{0-4}$-alkyl, aminocarbonyl, halo, and $NR^5R^6$;
$R^4$ is hydrogen, $C_{1-4}$ alkyl or —NR'R", wherein R' and R" each are independently selected from hydrogen, and $C_{1-4}$ alkyl;
and N oxides of such compounds.

2. A compound according to the general Formula Ia:

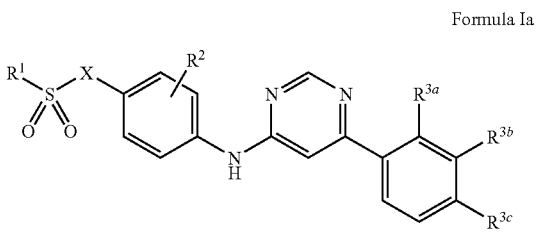

Formula Ia wherein
- $R^1$ is selected from the group consisting of —$NR^5R^6$, —$R^8$, —$C_{1-4}$ alkyl-OH, and —$C_{2-4}$-alkylene-O—$C_{1-4}$ alkyl;
- $R^5$ and $R^6$ independently of each other are selected from the group consisting of hydrogen, $C_{1-4}$ alkyl, $C_{2-4}$ alkenyl, hydroxy-$C_{1-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkylene, $C_{4-7}$ aryl-$C_{0-4}$ alkylene, and $C_{4-7}$ heteroaryl-$C_{0-4}$ alkylene, or alternatively wherein $R^5$ and $R^6$ together with the N-atom to which they are bound form a 5- to 8-membered heterocycloalkyl or a 5- to 6 membered heteroaryl;
- $R^8$ is $C_{1-4}$ alkyl, $C_{2-4}$ alkenyl, hydroxy-$C_{2-4}$ alkyl, $C_{3-8}$ cycloalkyl, $C_{3-8}$ cycloalkyl-$C_{1-4}$ alkyl or $C_{4-7}$ heterocycloalkyl-$C_{0-4}$ alkyl;
- X is methylene;
- wherein said cycloalkyl, heterocycloalkyl, aryl, heteroaryl or alkyl is further optionally substituted by up to 2 radicals selected from the group consisting of halo, hydroxy, $C_{1-4}$ alkyl, hydroxy-$C_{1-4}$ alkyl, $C_{1-4}$ alkyl-O—$C_{1-4}$ alkylene, $C_{1-4}$ alkyl-O—, and —$NR^5R^6$;
- $R^2$ can be 0 to 2 independent halo substituents;
- $R^{3a}$ is selected from the group consisting of hydrogen, $C_{1-4}$ alkoxy, $C_{1-4}$ alkenyloxy, aryl-$Cl_{1-4}$ alkoxy, and heteroaryl-$C_{1-4}$ alkoxy;
- $R^{3b}$ is selected from the group consisting of hydrogen, $C_{1-4}$ alkoxy, $C_{1-4}$ alkenyloxy, and $C_{0-4}$ alkylN$R^5R^6$;
- $R^{3c}$ is selected from the group consisting of hydrogen and halo;
- with the proviso that $R^{3a}$ and $R^{3b}$ cannot simultaneously be hydrogen;
- and N oxides of such compounds.

3. The compound of claim 2, wherein
- $R^1$ is selected from the group consisting of $NH_2$—, N-methyl-, N-propyl-, N-isopropyl-, N-cyclopropyl-, N-cyclopentyl-, and N,N-diethyl-,
- X is methylene;
- $R^2$ is hydrogen;
- $R^{3a}$ is selected from the group consisting of hydrogen, methoxy-, ethoxy-, isopropyloxy-, and benzyloxy-;
- $R^{3b}$ is selected from the group consisting of hydrogen, methoxy-, 3-Hydroxymethyl-piperidin-1-ylmethyl-, 3-Diethylaminomethyl-, 3-Piperidin-1-ylmethyl-, 3-Morpholin-4-ylmethyl-, 4-Methyl-piperazin-1-ylmethyl-, and [1,2,4]Triazol-1-ylmethyl-;
- $R^{3c}$ is hydrogen or halo;
- with the proviso that $R^{3a}$ and $R^{3b}$ cannot simultaneously be hydrogen;
- and N oxides of such compounds.

4. The compound of claim 3, selected from the group consisting of
- C-{4-[6-(2-Ethoxy-phenyl)-pyrimidin-4-ylamino]-phenyl}-N-propyl-methanesulfonamide (Compound 1);
- N-Cyclopentyl-C-{4-[6-(2-ethoxy-phenyl)-pyrimidin-4-ylamino]-phenyl}-methanesulfonamide (Compound 2);
- C-{4-[6-(2-Benzyloxy-phenyl)-pyrimidin-4-ylamino]-phenyl}-N-cyclopentyl-methanesulfonamide (Compound 3);
- C-{4-[6-(2-Benzyloxy-phenyl)-pyrimidin-4-ylamino]-phenyl}-N-isopropyl-methanesulfonamide (Compound 4);
- C-{4-[6-(2-Benzyloxy-phenyl)-pyrimidin-4-ylamino]-phenyl}-N-cyclopropyl-methanesulfonamide (Compound 5);
- {4-[6-(2-Ethoxy-phenyl)-pyrimidin-4-ylamino]-phenyl}-methanesulfonamide (Compound 6);
- C-{4-[6-(2-Ethoxy-phenyl)-pyrimidin-4-ylamino]-phenyl}-N-methyl-methanesulfonamide (Compound 7);
- {4-[6-(2-Benzyloxy-phenyl)-pyrimidin-4-ylamino]-phenyl}-methanesulfonamide (Compound 8);
- {4-[6-(2,3-Dimethoxy-phenyl)-pyrimidin-4-ylamino]-phenyl}-methanesulfonamide (Compound 9);
- N,N-Diethyl-C-{4-[6-(2-methoxy-phenyl)-pyrimidin-4-ylamino]-phenyl}-methanesulfonamide (Compound 10);
- C-{4-[6-(2-Benzyloxy-phenyl)-pyrimidin-4-ylamino]-phenyl}-N-methyl-methanesulfonamide (Compound 11);
- {4-[6-(3-Methoxy-phenyl)-pyrimidin-4-ylamino]-phenyl}-methanesulfonamide (Compound 12);
- {4-[6-(2-Methoxy-phenyl)-pyrimidin-4-ylamino]-phenyl}-methanesulfonamide (Compound 13);
- N-Cyclopentyl-C-{4-[6-(2-methoxy-phenyl)-pyrimidin-4-ylamino]-phenyl}-methanesulfonamide (Compound 14);
- N-Cyclopentyl-C-{4-[6-(2-isopropoxy-phenyl)-pyrimidin-4-ylamino]-phenyl}-methanesulfonamide (Compound 15);
- N-Cyclopentyl-C-{4-[6-(4-fluoro-2-methoxy-phenyl)-pyrimidin-4-ylamino]-phenyl}-methanesulfonamide (Compound 16);
- (4-{6-[3-(3-Hydroxymethyl-piperidin-1-ylmethyl)-phenyl]-pyrimidin-4-ylamino}-phenyl)-methanesulfonamide (Compound 17);
- {4-[6-(3-Diethylaminomethyl-phenyl)-pyrimidin-4-ylamino]-phenyl}-methanesulfonamide (Compound 18);
- {4-[6-(3-Piperidin-1-ylmethyl-phenyl)-pyrimidin-4-ylamino]-phenyl}-methanesulfonamide (Compound 19);
- {4-[6-(3-Morpholin-4-ylmethyl-phenyl)-pyrimidin-4-ylamino]-phenyl}-methanesulfonamide (Compound 20);
- (4-{6-[3-(4-Methyl-piperazin-1-ylmethyl)-phenyl]-pyrimidin-4-ylamino}-phenyl)-methanesulfonamide (Compound 21);
- {4-[6-(3-[1,2,4]Triazol-1-ylmethyl-phenyl)-pyrimidin-4-ylamino]-phenyl}-methanesulfonamide (Compound 22);
- N-Cyclopentyl-C-(4-{6-[3-(3-hydroxymethyl-piperidin-1-ylmethyl)-phenyl]-pyrimidin-4-ylamino}-phenyl)-methanesulfonamide (Compound 23);
- N-Cyclopentyl-C-{4-[6-(3-diethylaminomethyl-phenyl)-pyrimidin-4-ylamino]-phenyl}-methanesulfonamide (Compound 24);
- N-Cyclopentyl-C-{4-[6-(3-piperidin-1-ylmethyl-phenyl)-pyrimidin-4-ylamino]-phenyl}-methanesulfonamide (Compound 25);
- N-Cyclopentyl-C-{4-[6-(3-morpholin-4-ylmethyl-phenyl)-pyrimidin-4-ylamino]-phenyl}-methanesulfonamide (Compound 26);

N-Cyclopentyl-C-(4-{6-[3-(4-methyl-piperazin-1-ylmethyl)-phenyl]-pyrimidin-4-ylamino}-phenyl)-methanesulfonamide (Compound 27); and N-Cyclopentyl-C-{4-[6-(3-[1,2,4]triazol-1-ylmethyl-phenyl)-pyrimidin-4-ylamino]-phenyl}-methanesulfonamide (Compound 28).

5. A pharmaceutical preparation containing the compound of claim 1, together with a pharmaceutically acceptable carrier.

6. A method for the treatment of neuropathic pain, comprising administering a therapeutically effective amount of at least one of the compounds of claim 1 to a patient suffering from neuropathic pain.

7. A pharmaceutical preparation containing the compound of claim 2, together with a pharmaceutically acceptable carrier.

8. A method for the treatment of neuropathic pain, comprising administering a therapeutically effective amount of at least one compound of claim 2 to a patient suffering from neuropathic pain.

9. A pharmaceutical preparation containing the compound of claim 3, together with a pharmaceutically acceptable carrier.

10. A method for the treatment of neuropathic pain, comprising administering a therapeutically effective amount of at least one compound of claim 3 to a patient suffering from neuropathic pain.

11. A pharmaceutical preparation containing the compound of claim 4, together with a pharmaceutically acceptable carrier.

12. A method for the treatment of neuropathic pain, comprising administering a therapeutically effective amount of at least one compound of claim 4 to a patient suffering from neuropathic pain.

* * * * *

UNITED STATES PATENT AND TRADEMARK OFFICE
CERTIFICATE OF CORRECTION

| | | |
|---|---|---|
| PATENT NO. | : 8,389,521 B2 | Page 1 of 1 |
| APPLICATION NO. | : 12/451040 | |
| DATED | : March 5, 2013 | |
| INVENTOR(S) | : Heike Schauerte et al. | |

It is certified that error appears in the above-identified patent and that said Letters Patent is hereby corrected as shown below:

In the Claims

Column 58, Claim 1,
Line 56, before "alkoxy," (first occurrence) insert -- aryl-$C_{1-4}$ --.
Line 62, after "alkyl," (second occurrence) insert -- $C_{1-4}$-alkoxy, --.

Column 59, Claim 2,
Line 38, "aryl-$Cl_{1-4}$" should be -- aryl-$C_{1-4}$ --.
Lines 46 and 63, "N oxides" should be -- N-oxides --.

Signed and Sealed this
First Day of July, 2014

Michelle K. Lee
*Deputy Director of the United States Patent and Trademark Office*